(12) United States Patent
Pellegrini et al.

(10) Patent No.: US 10,500,252 B2
(45) Date of Patent: Dec. 10, 2019

(54) METHOD OF TREATING INTRACELLULAR INFECTION

(71) Applicant: Walter and Eliza Hall Institute of Medical Research, Parkville, Victoria (AU)

(72) Inventors: Marc Pellegrini, Parkville (AU); Gregor Klaus-Peter Ebert, Parkville (AU); Colin Glenn Begley, Westlake Village, CA (US)

(73) Assignee: WALTER AND ELIZA HALL INSTITUTE OF MEDICAL RESEARCH, Parkville, Victoria (AU)

( * ) Notice: Subject to any disclaimer, the term of this patent is extended or adjusted under 35 U.S.C. 154(b) by 0 days.

(21) Appl. No.: 14/899,581

(22) PCT Filed: Jun. 25, 2014

(86) PCT No.: PCT/AU2014/050092
§ 371 (c)(1),
(2) Date: Dec. 18, 2015

(87) PCT Pub. No.: WO2014/205516
PCT Pub. Date: Dec. 31, 2014

(65) Prior Publication Data
US 2016/0143995 A1    May 26, 2016

(30) Foreign Application Priority Data

Jun. 25, 2013  (AU) .................... 2013902327
Mar. 24, 2014  (AU) .................... 2014901029
May 26, 2014  (AU) .................... 2014901977

(51) Int. Cl.
*A61K 38/19*    (2006.01)
*A61K 45/06*    (2006.01)
(Continued)

(52) U.S. Cl.
CPC .......... *A61K 38/191* (2013.01); *A61K 31/404* (2013.01); *A61K 31/522* (2013.01);
(Continued)

(58) Field of Classification Search
CPC .............. A61K 31/407; A61K 31/4192; A61K 31/496; A61K 38/19; A61K 39/395; A61P 35/00; C07D 487/04
See application file for complete search history.

(56) References Cited

U.S. PATENT DOCUMENTS 3,832,253 A    8/1974  DiPalma et al.
3,854,480 A    12/1974 Zaffaroni
(Continued)

FOREIGN PATENT DOCUMENTS

JP    2012-513988 A    6/2012
JP    2013-519669 A    5/2013
(Continued)

OTHER PUBLICATIONS

Fulda et al., (Leukemia. 2012. 26; pp. 1155-1165).*
(Continued)

*Primary Examiner* — Jana A Hines
(74) *Attorney, Agent, or Firm* — Foley & Lardner LLP

(57) ABSTRACT

The present invention provides a method of treating an intracellular infection in a subject wherein the method comprising administering to the subject an IAP antagonist. In certain embodiments the IAP antagonist is a Smac mimetic.

24 Claims, 14 Drawing Sheets

(51) Int. Cl.
| | |
|---|---|
| A61K 31/404 | (2006.01) |
| A61K 31/522 | (2006.01) |
| A61K 31/713 | (2006.01) |
| C07K 14/47 | (2006.01) |
| A61K 38/05 | (2006.01) |
| A61K 38/17 | (2006.01) |
| C12N 15/113 | (2010.01) |

(52) U.S. Cl.
CPC ............ *A61K 31/713* (2013.01); *A61K 38/05* (2013.01); *A61K 38/1761* (2013.01); *A61K 38/19* (2013.01); *A61K 45/06* (2013.01); *C07K 14/4703* (2013.01); *C12N 15/1138* (2013.01); *C12N 2310/14* (2013.01); *C12N 2310/141* (2013.01); *C12N 2310/531* (2013.01); *C12N 2320/31* (2013.01); *C12N 2730/10171* (2013.01); *C12N 2740/16071* (2013.01)

(56) References Cited

U.S. PATENT DOCUMENTS

| | | | |
|---|---|---|---|
| 4,452,775 | A | 6/1984 | Kent |
| 4,667,014 | A | 5/1987 | Nestor, Jr. et al. |
| 4,748,034 | A | 5/1988 | de Rham |
| 5,239,660 | A | 8/1993 | Ooi |
| 5,705,109 | A | 1/1998 | Parks |
| 6,326,174 | B1 | 12/2001 | Joyce et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,589,118 | B2 | 9/2009 | Laurent et al. |
| 7,674,787 | B2 | 3/2010 | Wang et al. |
| 7,772,177 | B2 | 8/2010 | Jarvis et al. |
| 7,932,382 | B2 | 4/2011 | Wang et al. |
| 7,989,441 | B2 | 8/2011 | Chen et al. |
| 8,283,372 | B2 | 10/2012 | Condon et al. |
| 2004/0138119 | A1 | 7/2004 | Tamm et al. |
| 2005/0014712 | A1 | 1/2005 | Hansen et al. |
| 2008/0089896 | A1* | 4/2008 | Wang .................. A61K 38/191 424/158.1 |
| 2014/0303090 | A1 | 10/2014 | Condon et al. |

FOREIGN PATENT DOCUMENTS

| | | |
|---|---|---|
| JP | 2014-528409 A | 10/2014 |
| WO | 97/01633 A1 | 1/1997 |
| WO | 99/32619 A1 | 7/1999 |
| WO | 99/49029 A1 | 9/1999 |
| WO | 99/53050 A1 | 10/1999 |
| WO | 02/085946 A1 | 10/2000 |
| WO | 01/34815 A1 | 5/2001 |
| WO | 02/22175 A2 | 3/2002 |
| WO | 2009/025743 A2 | 2/2009 |
| WO | 2009/140447 A1 | 11/2009 |
| WO | WO-2010/074534 A2 | 7/2010 |
| WO | WO-2010/150836 A1 | 12/2010 |
| WO | WO-2011/102806 A1 | 8/2011 |
| WO | WO-2013/049350 A1 | 4/2013 |
| WO | 2013/071035 A1 | 5/2013 |

OTHER PUBLICATIONS

Woodman et al., 2007. The Natural History of Cervical HPV infection;Unresolved Issues. Medscape. (Year: 2007).*
Hamper et al., Mechanism of Persistent Herpes Simplex Virus Infection In Vitro. Journal of the National Cancer Institute, vol. 43, Issue 3, Sep. 1, 1969, pp. 621-634. (Year: 1969).*
Shanmugasundaram et al., Targeting Persistent Human Papillomavirus Infection. Viruses. Aug. 2017; 9(8): 229. (Year: 2017).*
Mitsuuchi et al., Cell Death Discovery Article No. 16046 (2017). (Year: 2017).*
Jul. 25, 2014—(WO) ISR and WO—App PCT/AU2014/050092.
2012—"Critical Role for Antiapoptotic Bcl-xL and Mcl-1 in Human Macrophage Survival and Cellular IAP1/2 (cIAP1/2) in Resistance to HIV-Vpr-induced Apoptosis"—Busca, A. et al—Journal of Biological Chemistry.
2009—"Altered regulation of extrinsic apoptosis pathway in HCV-infected HCC cells enhances susceptibility to mapatumumab-induced apoptosis"—Zhang, X. et al—Hepatology Research.
2012—"Inhibitor of apoptosis protein (IAP) antagonists inhibit anti-viral immunity by interfering with T cell expansion during LCMV infection"—Gentle, I.—Event at the University of Melbourne.
2006—"Manipulation of the nuclear factor-kB pathway and the innate immune response by viruses"—Hiscott, J. et al—Oncogene.
2011—"Proinflammatory cytokine TNF-a increases the stability of hepatitis B virus X protein through NF-kB signaling"—Shukla, R. et al.—Carcinogenesis.
Apr. 1, 2009—"Infectious Complications Associated with Monoclonal Antibodies and Related Small Molecules"—Salvana, E. et al—Clinical Microbiology Reviews (website).
2011—"XIAP antisense oligonucleotide (AEG35156) achieves target knockdown and induces apoptosis preferentially in CD34+? cells in a phase 1/2 study of patients with relapsed/refractory AML"—Carter, B. et al—Apoptosis.
1998—"Virus resistance and gene silencing in plants can be induced by simultaneous expression of sense and antisense RNA"—Waterhouse, P. et al—Proceedings of the National Academy of Sciences of the United States of America.
May 2005—RNA silencing and genome regulation—Almeida, R. et al—Trends in Cell Biology.
1995—"A DNA enzyme with Mg2+-dependent RNA phosphoesterase Activity"—Breaker, R. et al—Chemistry and Biology.
1997—"A general purpose RNA-cleaving DNA enzyme"—Santoro, S. et al—Proceedings of the National Academy of Sciences of the United States of America.
May 2, 2013—"Treatment of HCV Infection by Targeting MicroRNA"—Janssen, H. et al—The New England Journal of Medicine.
May 2013—"Hepatocyte-targeted RNAi Therapeutics for the Treatment of Chronic Hepatitis B Virus Infection"—Wooddell, C. et al—Molecular Therapy.
2000—"Smac, a Mitochondrial Protein that Promotes Cytochrome c-Dependent Caspase Activation by Eliminating IAP Inhibition"—Du C. et al—Cell Press.
Nov. 16, 2007—"IAP Antagonists Target cIAP1 to Induce TNFa-Dependent Apoptosis"—Vince, J. et al—Cell Press.
Feb. 24, 2012—"Inhibitor of Apoptosis Proteins Limit RIP3 Kinase-Dependent Interleukin-1 Activation"—Vince J. et al—Cell Press.
2010—"Manipulation of Host Cell Death Pathways during Microbial Infections"—Lamkanfi M et al—Cell Host and Microbe.
2011—"Dying to replicate: the orchestration of the viral life cycle, cell death pathways, and immunity"—Yatim N. et al—Immunity.
Dec. 23, 2012—"Viral infection and the evolution of caspase 8-regulated apoptotic and necrotic death pathways"—Mocarski E. et al—Nature Reviews Immunology.
May 18, 2010—"Hepatitis B virus core antigen determines viral persistence in a C57BL/6 mouse model"—Lin Y. et al—Proceedings of the National Academy of Sciences of the United States of America.
Nov. 21, 2006—"An immunocompetent mouse model for the tolerance of human chronic hepatitis B virus infection"—Huang L. et al—Proceedings of the National Academy of Sciences of the United States of America.
2011—"5' Triphosphorylated small interfering RNAs control replication of hepatitis B virus and induce an interferon response in human liver cells and mice"—Ebert, G. et al—Gastroenterology.
Aug. 2012—"Protection versus pathology in tuberculosis: recent insights"—Cooper, A. et al—Current Opinion in Immunology.
Jan. 2007—"Life and death in the granuloma: immunopathology of tuberculosis"—Saunders, B. et al—Immunology and Cell Biology.
2012—"Understanding latent tuberculosis: a moving target"—Lin, P. et al—The Journal of Immunology.

(56) References Cited

OTHER PUBLICATIONS

2011—"Modulation of cell death by M. tuberculosis as a strategy for pathogen survival"—Abebe, M.—Clinical and Developmental Immunology.
Sep. 2010—"Evasion of innate immunity by *Mycobacterium tuberculosis*: is death an exit strategy?"—Behar, S. et al—National Reveiws Microbiology.
Apr. 2010—"Escape of HIV-1-infected dendritic cells from TRAIL-mediated NK cell cytotoxicity during NK-DC cross-talk—a pivotal role of HMGB1"—Melki, M. et al—PLoS Pathogens.
2010—"To kill or be killed: how viruses interact with the cell death machinery"—Kaminskyy V. et al—Journal of Internal Medicine.
Jul. 2008—"HIV-1 viral genes and mitochondrial apoptosis"—Shedlock D. et al—Apoptosis.
2013—"Smac-Mimetic-Induced Epithelial Cell Death Reduces the Growth of Renal Cysts"—Fan, L. et al—Journal of the American Society of Nephrology.
Aug. 2011—"Azithromycin Treatment Modulates the Extracellular Signal-Regulated Kinase Mediated Pathway and Inhibits Inflammatory Cytokines and Chemokines in Epithelial Cells from Infertile Women with Recurrent Chlamydia trachomatis Infection"—Srivastava, P. et al—DNA and Cell Biology.
Feb. 2012—"Targeting IAP proteins for therapeutic intervention in cancer"—Fulda, S et al—Nature Reviews Drug Discovery.
Jan. 9, 2012—"Exploiting inhibitor of apoptosis proteins as therapeutic targets in hematological malignancies"—Fulda, S.—Leukemia.
Apr. 2011—"Modulation of NF-kB signalling by microbial pathogens"—Rahman, M. et al—Nature Reviews Microbiology.
2011—"Proinflammatory cytokine TNF-? increases the stability of hepatitis B virus X protein through NF-kB signaling"—Shukla, R—Carcinogenesis.
2000—"Gene expression: Total silencing by intron-spliced hairpin RNAs"—Smith, N. et al—Nature.
Jul. 2005—"Plant and animal microRNAs: similarities and differences"—Millar, A. et al—Functional & Integrative Genomics.
Apr. 2005—"MicroRNAs: a developing story"—Pasquinelli, A. et al.—Current Opinion in Genetics & Development.
2007—"Modulation of MAPK pathways and cell cycle byreplicating hepatitis B virus: factors contributing tohepatocarcinogenesis"—Chin R, et al—Journal of Hepatology.
2009—"New insights on the role of apoptosis and autophagy in HIV pathogenesis"—Gougeon M, et al—Apoptosis.
2008—"Is HIV infection a TNF receptor signalling-driven disease?"—Herbein G, et al.—Trends Immunology.
Dec. 29, 2015—International Preliminary Report on Patentabiltiy—App PCT/AU2014/050092.
"Exhibit 99.2—TetraLogic Corporate Presentation", (Apr. 2014) pp. 1-27. Retrieved from the Internet, URL: https://www.sec.gov/Archives/edgar/data/1361248/000110465914026238/a14-10136_1ex99d2.htm [retrieved on Nov. 2, 2016].
"PA BioWatch" Pennsylvania Bio, (Jan. 2014), pp. 1-16. Retrieved from the Internet, URL: http://www.actiatedmedical,com/WEBQ12014PABioWatchcompressed.
"TetraLogic Pharmaceuticals Announces Conference Call with Dr. March Pellegrini of the Walter and Eliza Hall Institute of Medical Research to Discuss TetraLogic Infectious Desease Program," TetraLogic Pharmaceuticals, (Jun. 2014) pp. 1-3. Retrieved from the Internet, URL: https://globenewswire.com/news-release/2014/06/13/643959/10085649/en/TetralLogic-Pharmaceuticals-Announces-Conference-Call-With-Dr-Marc-Pellegrini-of-the-Walter-and-Eliza-Hall-Institute-of-Medical-Research-to-Discuss-TetraLogic-Infectious-Disease-Pro.html [retrieved on Nov. 2, 2016].
Beug et al., "Modulation of immune signaling by inhibitors of apoptosis," Trends in Immunology, vol. 33, No. 11 (Nov. 2012) pp. 535-545.
Hougardy et al., "Proteasome inhibitor MG132 sensitizes HPV-positive human cervical cancer cells to rhTRAIL-induced apoptosis," International Journal of Cancer, vol. 118 (Apr. 2006) pp. 1892-1900.
Ling et al., "Oxymatrine induces human pancreatic cancer PANC-1 cells apoptosis via regulating expression of Bcl-2 and IAP families, and releasing of cytochrome c," Journal of Experimental & Clinical Cancer Research, vol. 30:66 (Jun. 2011) pp. 1-6.
Liu et al., "Cellular cIAP$_2$ Gene Expression Associated with Anti-HBV Activity of TNF-α in Hepatoblastoma Cells," Journal of Interferon & Cytokine Research, vol. 25 (Oct. 2005) pp. 617-626.
Ma et al. "Inhibition of Hepatitis B Virus and Induction of Hepatoma Cell Apoptosis by ASGPR-Directed Delivery of shRNAs," PLOS ONE (Oct. 2012) pp. 1-11.
Nachbur et al., "1127 Hepatitis B Virus Induces Loss of CIAP1 and Sensitivity to TNF-Alpha in Primary Hepatocytes," 46th Annual Meeting of the European-Association-for-the-Study-of-the-Liver (EASL), vol. 54, (Mar. 2011), p. S446.
Preethy et al., "Analysis of the Cytotoxic Potential of Anisomelic Acid Isolated from Anisomeles malabarica," Scientia Pharmaceutica, vol. 81, (Jan. 2013) pp. 559-566.
Preethy et al., "Novel action modality of the diterpenoid anisomelic acid causes depletion of E6 and E7 viral oncoproteins in HPV-transformed cervical carcinoma cells," Biochemical Pharmacology 89, (Feb. 2014) pp. 171-184.
Rajalingam et al., "IAP-IAP Complexes Required for Apoptosis Resistance of C. tracomatis-Infected Cells," PLoS Pathogens, vol. 2, No. 10 (Oct. 2006) pp. 1013-1023.
Supplementary European Search Report dated Apr. 5, 2017 in European Application No. 14818270 (EP 3013329).
Tan, "Human Papilloma Virus 16 E6 RNA Interference Enhances Cisplatin and Death Receptor-Mediated Apoptosis in Human Cervical Carcinoma Cells," Molecular Pharmacology, vol. 81, No. 5 (May 2012) pp. 701-709.
Wang et al., "Cellular, Biochemical, and Genetic Analysis of Mechanism of Small Molecule IAP Inhibitors," The Journal of Biological Chemistry, The American Society for Biochemistry and Molecular Biology, Inc., vol. 279, No. 46, (Nov. 2004) pp. 48168-41876.
Wang et al., "Inhibition of Hepatitis B Virus Replication by cIAP2 Involves Accelerating the Ubiquitin-Proteasome-Medicated Destruction of Polymerase," Journal of Virology, vol. 85, No. 21 (Nov. 2011) pp. 11457-11467.
Yuan et al., "Human papillomavirus type 16 E6 and E7 oncoproteins upregulate c-IAP2 gene expression and confer resistance to apoptosis," Oncogene vol. 24 (Jul. 2005) pp. 5069-5078.
Zane et al., "Clonal expansion of HTLV-1 positive CD8$^+$ cells relies on cIAP-2 but no on c-FLIP expression," Virology, Elsevier, vol. 407, (Nov. 2010) pp. 341-351.
Chun et al., "Latent reservoirs of HIV: Obstacles to the eradication of virus," Proc Natl. Acad. Sci. USA, vol. 96 (Sep. 1999) pp. 10958-10961.
Ebert et al. "Eliminating hepatitis B by antagonizing cellular inhibitors of apoptosis," Proc. Nat. Acad. Sci. USA, vol. 112, No. 18, (May 2015) pp. 5803-5808.
Ebert et al., "Cellular inhibitor of apoptosis proteins prevent clearance of hepatitis B virus," Proc. Nat. Acad. Sci. USA, vol. 112, No. 18 (May 2015) pp. 5797-5802.
Nutter et al. "Long-term control of HIV by CCR5 Delta32/Delta32 stem-cell transplantation," New Engl. J. Med. vol. 360, No. 7 (Feb. 2009) pp. 692-698.
Lee et al. "Macrophage Apoptosis in Tuberculosis," Yonsei Med J. vol. 50, No. 1 (2009) pp. 1-11.
Nixon et al. "In vivo models of human immunodeficiency virus persistence and cure strategies," J. Infectious Diseases, vol. 215, No. S3 (2017) pp. S142-S151.
Pache et al. "BIRC2/cIAP1 is a negative regulator of HIV-1 transcription and can be targeted by Smac mimetics to promote reversal of viral latency," Cell Host & Microbe (Sep. 2015) vol. 18, pp. 345-353.
Pedroza-Roldan et al. "Recent mouse models and vaccine candidates for preventing chronic/latent tuberculosis infection and its reactivation," Pathogens and Disease, vol. 75 (Jul. 2017).
Preston et al. "Hydrodynamic injection as a method of gene delivery in mice: a model of chronic hepatitis B virus infection." Programmed Cell Death: Methods and Protocols, Methods in Molecular Biology, vol. 1419, (2016) DOI 10.1007/978-1-4939-3581-9_9.

(56) References Cited

OTHER PUBLICATIONS

Sampey et al. "The SMAC mimetic AZD5582 is a potent HIV latency reversing agent." bioRxiv (May 2, 2018) http://dx.doi.org/10.1101/312447.
White, et al. "Latent herpesvirus infection arms NK cells." Blood, vol. 115, No. 22 (Jun. 2010) pp. 4377-4383.
Zhang et al. "Quantifying residual HIV-1 replication in patients receiving combination antiretroviral therapy." New Engl. J. Med., vol. 340, No. 21 (May 1999) pp. 1605-1613.
Akihiko, "MHC class I," 1998-2000 Specific Area Research Grants-in-Aid for Scientific Research, Research Report, Basic Research for Controlling Aids (2004) pp. 189-191.
Busca et al., "Critical Role for Antiapoptotic Bcl-xL and Mcl-1 in Human Macrophage Survival and Cellular IAP1/2 (cIAP1/2) in Resistance to HIV-Vpr-induced Apoptosis," Journal of Biochemistry, (Apr. 2012) vol. 287 No. 18, pp. 15118-15133.
Japanese Office Action dated Apr. 23, 2018 in JP Application No. 2016-522137 with English translation.
Ma et al., "Abstract 1939: TL32711, a novel Smac mimetic, exerts significant antitumor efficacy in primary pancreatic adenocarcinoma model," Cancer Research, (Apr. 2012) vol. 72 Issue 8 Supplement.
Smith et al., "Abstract 3857: Smac mimetic TL32711 and TRAIL synergistically induce apoptosis of germinal center B lymphoma cells," Cancer Research, (Apr. 2012) vol. 72 Issue 8 Supplement.
Smith et al., "Birinapant (TL32711), a Small Molecule Smac Mimetic, Induces Regressions in Childhood Acute Lymphoblastic Leukemia (ALL) Xenografts That Express TNFα and Synergizes with TNFα in Vitro—A Report From the Pediatric Preclinical Testing Program (PPTP)," Blood, 2012, vol. 120 Issue 21, p. 3565.
Takamatsu et al., "Inhibition of Akt/GSK3β signaling pathway by Legionella pneumophila is involved in induction of T-cell apoptosis," Biochem. J., (2010) vol. 427, pp. 57-67.
"Chapter 15: Patterns of Infection: a Delicate Balance," Microbiology, (1999) pp. 518-551.
Agosto et al., "HIV-1-Infected CD4+ T Cells Facilitate Latent Infection of Resting CD4+ T Cells through Cell-Cell Contact," Cell Reports, vol. 24 pp. 2088-2100 (Aug. 2018).
Alizon et al., "Why Human Papillomavirus Acute Infections Matter," Viruses (2017), vol. 9, No. 293, pp. 1-18.
Boldogh et al., "Chapter 46: Persistent Viral Infections", Medical Microbiology, 4th Edition (1996).
Bowie, "Viral Appropriation of Apoptotic and NF-kb Signaling Pathways," Journal of Cellular Biochemistr, vol. pp. 1099-1108 (2004).
Campbell et al., "SMAC Mimetics Induce Autophagy-Dependent Apoptosis of HIV-1-Infected Resting Memory CD4+ T Cells," Cell Host & Microbe, vol. 24, pp. 689-702 (Nov. 2018).
Chun et al., "Early establishment of a pool of latently infected, resting CD4+ T cells during primary HIV-1 infection," Proc. Natl. Acad. Sci., vol. 95, pp. 8869-8873 (Jul. 1998).
Ciuffi et al., "The benefits of integration," Clin. Microbiol. Infect. (2016) vol. 22, pp. 324-332.
Ebert, "Cellular inhibitor of apoptosis proteins prevent clearance of hepatitis B virus," PNAS (May 2015) vol. 112, No. 18, pp. 5797-5802.
Flynn et al., "Tuberculosis: Latency and Reactivation," Infection and Immunity, (Jul. 2001), pp. 4195-4201.
Huang et al., "An immunocompetent mouse model for the tolerance of human chronic hepatitis B virus infection," PNAS (Nov. 2006) vol. 103, No. 47.
Kroon et al., "Acute HIV infection detection and immediate treatment estimated to reduce transmission by 89% among men who have sex with men in Bangkok," Journal of the International AIDS Society (2017) vol. 20, No. 21708, pp. 1-9.

Nixon et al., "In Vivo Models of Human Immunodeficiency Virus Persistence and Cure Strategies," The Journal of Infectious Diseases, (2017), vol. 215, (Suppl 3), pp. S142-S151.
Pace et al., "HIV reservoirs and latency models," Virology 411 (2011), pp. 344-354.
Pistello et al., "Integration of the viral genome into the host cell genome: a double-edged sword," (published online Feb. 2016) Clin. Microbiol. Infect. (2016), No. 22, pp. 296-298.
Satheesan,"HIV Replication and Latency in a Humanized NSG Mouse Model during Suppressive Oral Combination Antiretroviral Therapy," Journal of Virology, (Apr. 2018) vol. 92, No. 7, e02118-17, pp. 1-20.
Virgin et al., "Redefining Chronic Viral Infection," Cell, vol. 138 (Jul. 2009).
Deruaz et al., "Humanized mouse models of latent HIV infection," Curr. Opinion in Virology, vol. 25 (2017) pp. 97-104.
Tamanini et al., "Discovery of a Potent Nonpeptidomimetic, Small-Molecule Antagonist of Cellular Inhibitor of Apoptosis Protein 1 (cIAP1) and X-Linked Inhibitor of Apoptosis Protein (XIAP)," Journal of Medical Chemistry, vol. 60, pp. 4611-4625 (May 2017).
Ward et al., "ASTX660, a novel non-peptidomimetic antagonist of cIAP1/2 and XIAP, potently induces TNF-α dependent apoptosis in cancer cell lines and inhibits tumor growth," (Published Online on Apr. 25, 2018).
Cooper et al., "Mouse Model of Tuberculosis," Cold Spring Harb Perspect Med (2015) 5, a018556, pp. 1-8.
Fulda, "Exploiting inhibitor of apoptosis proteins as therapeutic targets in hematological malignancies," Leukemia (2012) 26, p. 1155-1165.
Gomez et al., "M. tuberculosis persistence, latency, and drug tolerance," Tuberculosis (2004) 84, pp. 29-44.
Guo et al., "Animal models for the study of hepatitis B virus infection," Zoological Research, vol. 39, No. 1, pp. 25-31 (2018).
Stager et al., "Immune evasive mechanisms contributing to persistent Leishmania donovani infection," Immunol Res (2010) vol. 47, pp. 14-24.
Yu et al., "Immunology (non-medical)", Central China Normal University Press, pp. 163-165 (Aug. 2008).
Yulish et al., "Persistent infections in humans. Strategy of Relations," Child's Health, No. 4. (19), (2009).
Chinese Office Action dated Dec. 18, 2018 in Chinese Application No. 201480036777.1.
Eurasian Office Action dated Jan. 2019 in Eurasian Application No. 201690075/28.
Abu-Zant et al., "Incomplete Activation of Macrophage Apoptosis during Intracellular Replication of Legionella pneumophila," Infection and Immunity, vol. 73, No. 9, pp. 5339-5349 (Sep. 2005).
Teijaro et al., "Persistent LCMV Infection is Controlled by Blockade of Type I Interferon Signaling," Science, vol. 340, No. 6129, pp. 204-211 (Apr. 2013).
Ting et al., "More to Life than NF-kB in TNFR1 Signaling," Trends in Immunology, vol. 37, No. 8, pp. 535-545 (Aug. 2016).
Xiao et al., "NF-kB Activation is Not Required for Chlamydia trachomatis Inhibition of Host Epithelial Cell Apoptosis," The Journal of Immunology, vol. 174, No. 3, pp. 1701-1708 (Jan. 2005).
Yuan et al., "Modulation of Apoptotic Pathways by Human Papillomaviruses (HPV): Mechanisms and Implications for Therapy," Viruses, vol. 4, No. 12, pp. 3831-3850 (Dec. 2012).
"HIV-1 Nef," Minophagen Medical Review, vol. 44, No. 2, pp. 61-70 (Mar. 1999).
Brumme et al., Marked Epitope- and Allele-Specific Differences in Rates of Mutation in Human Immunodeficiency Type 1 (HIV-1) Gag, Pol, and Nef Cytotoxic T-Lymphocyte Epitopes in Acute/Early HIV-1 Infection, Journal of Virology, vol. 82, No. 18 (Sep. 2008).
Pre-Appeal Examination Report dated Aug. 5, 2019 in Japanese Application No. 2016-522137.

* cited by examiner

METHOD OF TREATING INTRACELLULAR INFECTION

CROSS-REFERENCE TO RELATED APPLICATIONS

This application is a U.S. National Stage application under 35 U.S.C. § 371 of International Application PCT/AU2014/050092 (published as WO 2014/205516 A1), filed Dec. 31, 2014, which claims priority to Application AU 2013902327, filed Jun. 25, 2013, Application AU 2014901029, filed Mar. 24, 2014, and Application AU 2014901977, filed May 26, 2014. Benefit of the filing date of each of these prior applications is hereby claimed. Each of these prior applications are hereby incorporated by reference in its entirety.

FIELD OF INVENTION

The present invention relates to a method of treating intracellular infections. The method involves the administration of an Inhibitor of Apoptosis (IAP) antagonist.

BACKGROUND OF INVENTION

Chronic overwhelming infections by pathogens such as hepatitis B virus (HBV), human immunodeficiency virus (HIV), Human papilloma virus (HPV), *Mycobacterium tuberculosis, Histoplasma* spp. and *Plasmodium* spp. are associated with a deficiency in pathogen-specific immunity and an aberrant non-specific inflammatory response that is deleterious in causing collateral host cell damage. Whilst various treatment strategies have been developed over the years, they have had little impact.

Hepatitis B is a common disease with a worldwide distribution, with an estimated 280,000,000 as being carriers of HBV. Globally, HBV infection is most common in the developing countries of Southeast Asia, Africa and parts of South America, where vertical transmission to infants at an early age results in a high proportion of infected individuals becoming chronic carriers of HBV. Males acquiring HBV as infants have approximately a 40% chance of dying from cirrhosis or primary hepatocellular carcinoma as a result of chronic HBV infection. By contrast, females infected at birth have about a 15% chance of dying a similar death from chronic hepatitis B infection.

Hepatitis B infection remains difficult to treat despite several drugs now in clinical use, including interferon α2b (IFN α2b), IFN α2a, lamivudine, adefovir and entecavir. Treatment is either ineffective at the outset, or can become so by the emergence of drug resistant viruses. Existing drug regimens have also been known to suffer from being long-term, expensive and associated with undesirable side effects. For example, while lamivudine has been applied with some success in the treatment of HBV infection, it is associated with an increasing risk of resistance, which can be as high as 45-55% after the second year of treatment. Moreover, HBV cannot be completely eliminated from the liver under such therapy, so that reactivation of a HBV infection occurs in many cases even after cessation a treatment. When end-stage liver failure occurs in patients with chronic HBV infection, liver transplantation is the only alternative form of treatment. However, as HBV infection persists, the graft can become infected, thus limiting patient and graft survival.

Human immunodeficiency virus/acquired immunodeficiency syndrome (HIV/AIDS) also represents a global health crisis, particularly in developing countries. The use of anti-retroviral drugs has significantly changed the expectancy and quality of life of HIV infected individuals. However, in spite of such anti-retroviral drug intervention, persistent immune activation, CD4 T cell and B cell decay and loss of immune function are only partially reverted. Patients are also at risk of non-AIDS defining illnesses and causes of death, such as cancer, cardiovascular disease, liver and kidney failure, central nervous system disorders (e.g., toxoplasma encephalitis) and persistent infections.

The present invention is concerned with the development of a novel approach to the treatment of intracellular infections.

SUMMARY OF INVENTION

Accordingly, in a first aspect, the present invention provides a method of treating an intracellular infection in a subject, the method comprising administering to the subject an IAP antagonist.

DETAILED DESCRIPTION OF THE INVENTION

Figure 1:
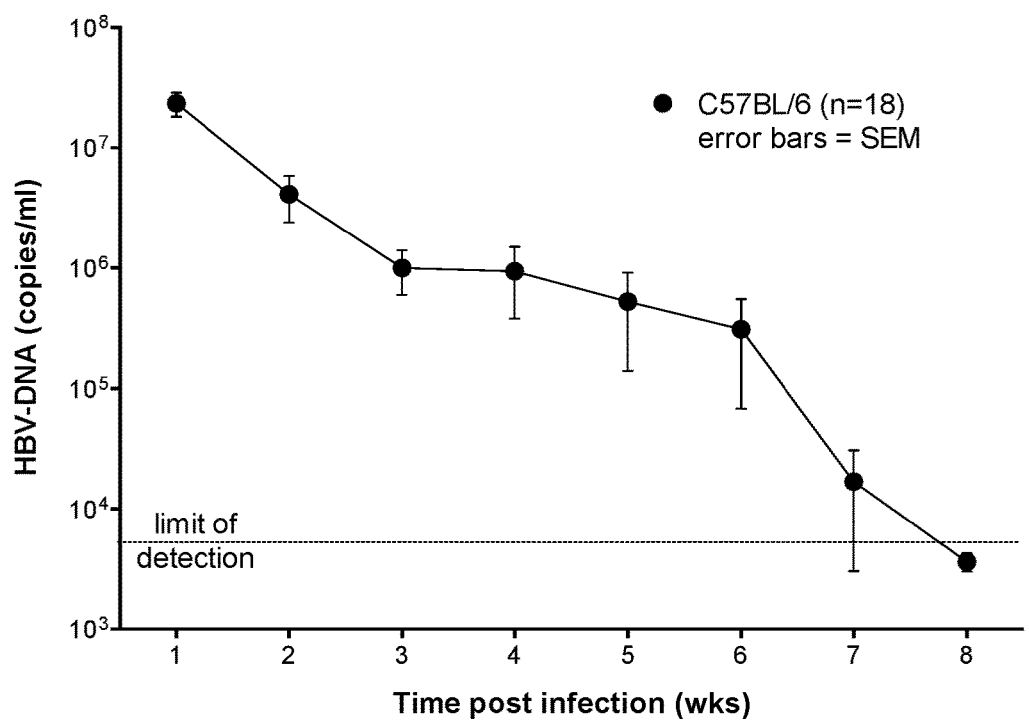
FIG. 1 shows the time course of serum HBV DNA levels in the serum of infected mice over a 8 week period (top panel). Bottom panels shows EM micrographs of virions (left) and subviral particles (right) in serum.
Figure 1:
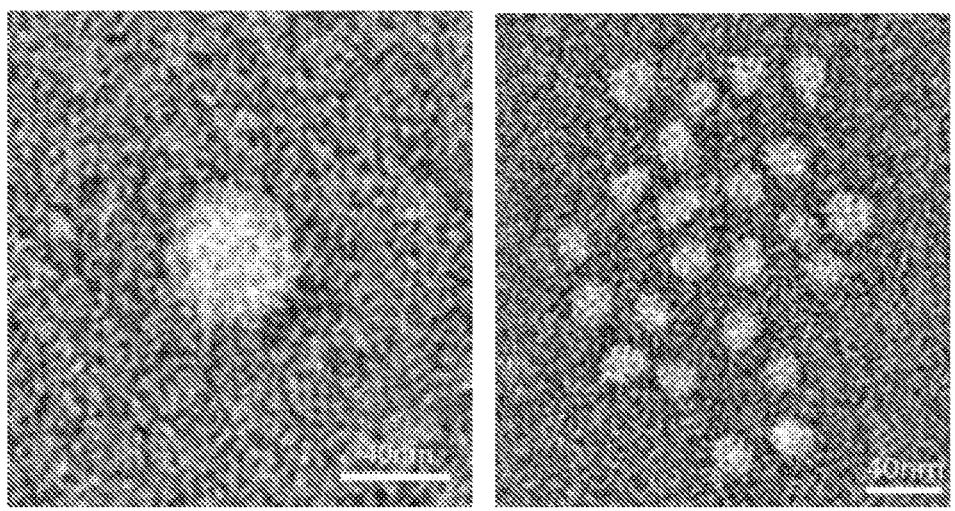

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavor to which this specification relates.

All publications mentioned in this specification are herein incorporated by reference in their entirety.

It must be noted that, as used in the subject specification, the singular forms "a", "an" and "the" include plural aspects unless the context clearly dictates otherwise. Thus, for example, reference to "an agent" includes a single agent, as well as two or more agents; reference to "a molecule" includes a single molecule, as well as two or more molecules; and so forth.

A mechanism for eradicating pathogens is for infected cells to activate the process of programmed cell death. This kills both pathogen and infected cell and prevents the spread of the microbe. However, many pathogens have developed strategies to prevent their host cell from committing suicide. A group of molecules in host cells, called Inhibitor of Apoptosis Proteins (IAPs), have several roles in regulating the cell death program and in modulating inflammation.

The present invention is predicated, in part, on the finding that, by antagonizing IAPB in vivo, the clearance of persistently infected host cells and the elimination of pathogens is enhanced without causing overt deleterious collateral damage to the host. This may be achieved by use of pan-IAP antagonist, which may be a pan-cIAP antagonist, e.g., a cIAP1 and/or cIAP2 antagonist.

Accordingly, in a first aspect, the present invention provides a method of treating an intracellular infection in a subject, the method comprising administering to the subject an IAP antagonist.

As used herein the term "treating" means that the level or number of pathogens responsible for the intracellular infection in the organism being treated, e.g., the human patient, is reduced.

The IAP family of proteins includes XIAP (BIRC4), cIAP1 (BIRC2), cIAP2 (BIRC3); NAIP (BIRC1), Survivin (BIRC5), Apollon (Bruce; BIRC6), ML-IAP (BIRC7; Livin, KIAP) and ILP2 (BIRC8). There is a degree of redundancy between family members, but targeted compound deletion of XIAP+cIAP1+cIAP2 causes early embryonic lethality in mice. These molecules promote inflammation and abrogate cell death signalling1. The present inventors have shown, for the first time, that IAPB play an important role in maintaining persistent intracellular infection in a host.

In an embodiment, the IAP is cIAP1 or cIAP2, or both.

cIAP1 is encoded by the sequence shown in GenBank DQ068066.1. Transcript variants of cIAP1 include NCBI reference sequences NM_001166.4, NM_001256163.1 and NM_001256166.1.

cIAP2 is encoded by the sequence shown in GenBank BC037420.1. Transcript variants of cIAP2 include NCBI reference sequences NM_001165.4 and NM_182962.2.

XIAP (X-linked inhibitor of apoptosis) is encoded by GenBank NCBI reference sequence NG_007264.1. Transcript variants of XIAP include NCBI reference sequences NM_001167.3, NM_001204401.1 and NR_037916.1.

Suitable IAP antagonists would be known to persons skilled in the art. Examples include the monovalent IAP antagonists GDC-0145, GDC-0152, and GDC-0917 (Genentech, USA), AT-IAP (Astex, UK), and AT-406 (Ascenta, USA) and the bivalent IAP antagonists AEG40826 (Aegera Therapeutics, USA), SM-1200 (Univ. of Michigan), HGS1029 (Human Genome Sciences, USA), BV6 (Genentech, USA), AEG40730 (Aegera Therapeutics); SM-164 (Univ. of Michigan); CS3 (Genentech); ML101 (Sanford-Burnham Medical Research Institute); AEG35156 (Aegera Therapeutics) and birinapant/TL32711 (TetraLogic, USA). Several of these are further discussed in Fulda and Vucic (*Nature Reviews Drug Discovery*, 2012, vol 11, 109-124) and Fulda (*Leukemia*, 2012, vol 26, 1155-1165), the contents of which are incorporated herein by reference. Whilst it is currently believed that both monovalent and bivalent IAP antagonists can be used in the present invention it is presently preferred that the IAP antagonist is bivalent.

In an embodiment, the IAP antagonist is a mimetic of second mitochondria-derived activator of caspase (Smac). Smac is a pro-apoptotic mitochondrial protein that is an endogenous inhibitor of IAPB. Smac mimetics have been shown to stimulate programmed cell death and thus have become a focus in the development of novel cancer therapeutics[2,3].

Smac antagonises IAP-mediated caspase inhibition by direct interaction with IAPB and/or induces proteasomal degradation of some members of the IAP family (cIAP1 and cIAP2). The ability of Smac to promote both the proteolytic activation of pro-caspase-3 and the enzymatic activity of mature caspase-3 depends on its ability to specifically interact with IAP. Smac binds to the BIR1/BIR2 linker region and BIR3 of XIAP disrupting the inhibition of caspase-3 and -7 and caspase-9 thus facilitating apoptosis or programmed cell death. Smac and Smac mimetics also induce proteasomal degradation of cIAP1 and cIAP2 resulting in the inhibition of canonical NF-κB activation. Many viruses modulate NF-κB activation to promote disease pathogenesis (Reference: Rahman and McFadden, *Nat Rev Microbio* 2011 9:291-306; Hiscott et al *Oncogene* 2006 25:6844-67; Shukla et at *Carcinogenesis* 201132:978-985). Without being bound to a particular understanding of the mechanism underlying this invention, these activities suggest a mechanism whereby Smac mimetics could be used in the treatment of such infections.

The discovery of Smac mimetics was enabled by the elucidation of the crystal structure of the interaction between Smac and IAPB. Smac mimetics appear to facilitate apoptotic cell death in tumour cells through multiple mechanisms, including binding directly to and antagonising IAPB, eliminating IAPB by promoting autoubiquitylation and proteasomal degradation of cIAPs and activation of a cell's extrinsic apoptotic pathway through TNF stimulation. TNF is a critical cytokine required for the control of many infections and when TNF is antagonized, for the treatment of autoimmune disorders, many latent infections reactivate (see http://cmr.asm.org/content/22/2/274.full#sec-49). As a corollary, promotion of TNF activity in these infections may promote their clearance.

Examples of Smac peptidomimetics, including some of those identified above, are disclosed in, without limitation, U.S. Pat. No. 7,517,906; 7,419,975; 7,589,118; 7,932,382; 7,345,081; 7,244,851; 7,674,787; 7,772,177; 7,989,441; US20100324083; US20100056467; US20090069294; US20110065726; US20110206690; WO2011098904, all of which are incorporated herein by reference as though fully set forth. The compounds disclosed therein, and Smac mimetics generally, have the structure:

[P1-P2-P3-P4]     (Formula I)

or

[P1-P2-P3-P4]-L-[P1'-P2'-P3'-P4']     (Formula II)

wherein P1-P2-P3- and P1'-P2'-P3'- correspond to peptide replacements, i.e., peptidomimetics, of the N-terminal Ala-Val-Pro-tripeptide of mature Smac and P4 and P4' correspond to amino acid replacements of the fourth N-terminal amino acid, Phe, Tyr, Ile, or Val, and L is a linking group or bond covalently linking [P1-P2-P3-P4] to [P1'-P2'-P3'-P4'].

For example, without limitation, a Smac mimetic may reside in the following genus of compounds of Formula II:
P1 and P1' are $NHR^1$—$CHR^2$—$C(O)$—;
P2 and P2' are —NH—$CHR^3$—$C(O)$—;
P3 and P3' are pyrrolidine, pyrrolidine fused to a cycloalkyl, or pyrrolidine fused to a heterocycloalkyl having a —N— heteroatom, optionally substituted in each case, and wherein the pyrrolidine of P3/P3' is bound to P2/P2' by an amide bond;
P4 and P4' are -M-$Q_p$-$R^7$.
The variable substituents can be, for example:
$R^1$: —H or —$CH_3$;
$R^2$: —$CH3$, —$CH2CH3$ or —$CH2OH$;
$R^3$: C2-6 alkyl, C2-6 alkoxy, C3-C6 cycloalkyl or heterocycloalkyl, or C6-C8 aryl or heteroaryl, optionally substituted in each case;
M: a covalent bond, C1-6 alkylene, substituted C1-C6 alkylene such as but not limited to —C(O)—;
Q: a covalent bond, C1-6 alkylene, substituted C1-C6 alkylene, —O— or —$NR^8$—,
P: 0 or 1;
$R^7$: cycloalkyl, cycloalkylaryl, alkylaryl, alkylheteroaryl, aryl or heteroaryl, optionally substituted in each case;
$R^8$: —H or C1-6 alkyl.
L is a linking group or bond covalently linking [P1-P2-P3-P4] to [P1'-P2'-P3'-P4'].

"Alkyl" (monovalent) and "alkylene" (divalent) when alone or as part of another term (e.g., alkoxy) mean branched or unbranched, saturated aliphatic hydrocarbon group, having up to 12 carbon atoms unless otherwise specified. Examples of particular alkyl groups include, but are not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The term, "lower," when used to modify alkyl, alkenyl, etc., means 1 to 4 carbon atoms, branched or linear so that, e.g., the terms "lower alkyl", "$C_1$-$C_4$ alkyl" and "alkyl of 1 to 4 carbon atoms" are synonymous and used interchangeably to mean methyl, ethyl, 1-propyl, isopropyl, 1-butyl, sec-butyl or t-butyl. Examples of alkylene groups include, but are not limited to, methylene, ethylene, n-propylene, n-butylene and 2-methyl-butylene.

The term substituted alkyl refers to alkyl moieties having substituents replacing one or more hydrogens on one or more (often no more than four) carbon atoms of the hydrocarbon backbone. Such substituents are independently selected from the group consisting of: a halogen (e.g., I, Br, Cl, or F, particularly fluoro(F)), hydroxy, amino, cyano, mercapto, alkoxy (such as a $C_1$-$C_6$ alkoxy, or a lower ($C_1$-$C_4$)alkoxy, e.g., methoxy or ethoxy to yield an alkoxyalkyl), aryloxy (such as phenoxy to yield an aryloxyalkyl), nitro, oxo (e.g., to form a carbonyl), carboxyl (which is actually the combination of an oxo and hydroxy substituent on a single carbon atom), carbamoyl (an aminocarbonyl such as $NR_2C(O)$—, which is the substitution of an oxo and an amino on a single carbon atom), cycloalkyl (e.g., a cycloalkylalkyl), aryl (resulting for example in aralkyls such as benzyl or phenylethyl), heterocyclylalkyl (e.g., heterocycloalkylalkyl), heteroaryl (e.g., heteroarylalkyl), alkylsulfonyl (including lower alkylsulfonyl such as methyl sulfonyl), arylsulfonyl (such as phenylsulfonyl), and —$OCF_3$ (which is a halogen substituted alkoxy). The invention further contemplates that several of these alkyl substituents, including specifically alkoxy, cycloalkyl, aryl, heterocyclyalkyl and heteroaryl, are optionally further substituted as defined in connection with each of their respective definitions provided below. In addition, certain alkyl substituent moieties result from a combination of such substitutions on a single carbon atom. For example, an ester moiety, e.g., an alkoxycarbonyl such as methoxycarbonyl, or tert-butoxycarbonyl (Boc) results from such substitution. In particular, methoxycarbonyl and Boc are substituted alkyls that result from the substitution on a methyl group (—$CH_3$) of both an oxo (=O) and an unsubstituted alkoxy, e.g., a methoxy ($CH_3$—O) or a tert-butoxy (($CH_3$)$_3$C—O—), respectively replacing the three hydrogens. Similarly, an amide moiety, e.g., an alkylaminocarbonyl, such as dimethlyaminocarbonyl or methylaminocarbonyl, is a substituted alkyl that results from the substitution on a methyl group (—$CH_3$) of both an oxo (=O) and a mono-unsubstitutedalkylamino or, diunsubstitutedalkylamino, e.g., dimethylamino (—N—($CH_3$)$_2$), or methylamino (—NH—($CH_3$)) replacing the three hydrogens (similarly an arylaminocarbonyl such as diphenylaminocarbonyl is a substituted alkyl that results from the substitution on a methyl group (—$CH_3$) of both an oxo (=O) and a mono-unsubstitutedaryl(phenyl)amino). Exemplary substituted alkyl groups further include cyanomethyl, nitromethyl, hydroxyalkyls such as hydroxymethyl, trityloxymethyl, propionyloxymethyl, aminoalkyls such as aminomethyl, carboxylalkyls such as carboxymethyl, carboxyethyl, carboxypropyl, 2,3-dichloropentyl, 3-hydroxy-5-carboxyhexyl, acetyl (e.g., an alkanoyl, where in the case of acetyl the two hydrogen atoms on the —$CH_2$ portion of an ethyl group are replaced by an oxo (=O)), 2-aminopropyl, pentachlorobutyl, trifluoromethyl, methoxyethyl, 3-hydroxypentyl, 4-chlorobutyl, 1,2-dimethyl-propyl, pentafluoroethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), cycloalkylcarbonyl (e.g., cuclopropylcarbonyl) and 2-carbamoyloxyethyl. Particular substituted alkyls are substituted methyl groups. Examples of substituted methyl group include groups such as hydroxymethyl, protected hydroxymethyl (e.g., tetrahydropyranyl-oxymethyl), acetoxymethyl, carbamoyloxymethyl, trifluoromethyl, chloromethyl, carboxymethyl, carboxyl (where the three hydrogen atoms on the methyl are replaced, two of the hydrogens are replaced by an oxo (=O) and the other hydrogen is replaced by a hydroxy (—OH)), tert-butoxycarbonyl (where the three hydrogen atoms on the methyl are replaced, two of the hydrogens are replaced by an oxo (=O) and the other hydrogen is replaced by a tert-butoxy (—O—C(CH$_3$)$_3$), bromomethyl and iodomethyl. When the specification and especially the claims refer to a particular substituent for an alkyl, that substituent can potentially occupy one or more of the substitutable positions on the alkyl. For example, reciting that an alkyl has a fluoro substituent, would embrace mono-, di-, and possibly a higher degree of substitution on the alkyl moiety.

The term substituted alkylene refers to alkylene moieties having substituents replacing one or more hydrogens on one or more (often no more than four) carbon atoms of the hydrocarbon backbone where the alkylene is similarly substituted with groups as set forth above for alkyl.

Alkoxy is —O-alkyl. A substituted alkoxy is —O-substituted alkyl, where the alkoxy is similarly substituted with groups as set forth above for alkyl. One substituted alkoxy is acetoxy where two of the hydrogens in ethoxy (e.g., —O—CH$_2$—CH$_3$) are replaced by an oxo, (=O) to yield —O—C(O)—CH$_3$; another is an aralkoxy where one of the hydrogens in the alkoxy is replaced by an aryl, such as benzyloxy, and another is a carbamate where two of the hydrogens on methoxy (e.g., —O—CH$_3$) are replaced by oxo (=O) and the other hydrogen is replaced by an amino (e.g., —NH$_2$, —NHR or —NRR) to yield, for example, —O—C(O)—NH$_2$. A lower alkoxy is —O-lower alkyl.

"Alkenyl" (monovalent) and "alkenylene" (divalent) when alone or as part of another term mean an unsaturated hydrocarbon group containing at least one carbon-carbon double bond, typically 1 or 2 carbon-carbon double bonds, which may be linear or branched and which have at least 2 and up to 12 carbon atoms unless otherwise specified. Representative alkenyl groups include, by way of example, vinyl, allyl, isopropenyl, but-2-enyl, n-pent-2-enyl, and n-hex-2-enyl.

The terms substituted alkenyl and substituted alkenylene refer to alkenyl and alkenylene moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as C$_1$-C$_6$ alkoxy), aryloxy (such as phenoxy), nitro, mercapto, carboxyl, oxo, carbamoyl, cycloalkyl, aryl, heterocyclyl, heteroaryl, alkylsulfonyl, arylsulfonyl and —OCF$_3$.

"Alkynyl" means a monovalent unsaturated hydrocarbon group containing at least one carbon-carbon triple bond, typically 1 carbon-carbon triple bond, which may be linear or branched and which have at least 2 and up to 12 carbon atoms unless otherwise specified. Representative alkynyl groups include, by way of example, ethynyl, propargyl, and but-2-ynyl.

"Cycloalkyl" when alone or as part of another term means a saturated or partially unsaturated cyclic aliphatic hydrocarbon group (carbocycle group), having 3 to 8 carbon atoms unless otherwise specified, such as cyclopropyl, cyclobutyl, cyclopentyl and cyclohexyl, and further includes polycyclic, including fused cycloalkyls such as 1,2,3,4-tetrahydonaphthalenyls (1,2,3,4-tetrahydonaphthalen-1-yl, and 1,2,3,4-tetrahydonaphthalen-2-yl), indanyls (indan-1yl, and indan-2-yl), isoindenyls (isoinden-1-yl, isoinden-2-yl, and isoinden-3-yl) and indenyls (inden-1-yl, inden-2-yl and inden-3-yl). A lower cycloalkyl has from 3 to 6 carbon atoms and includes cyclopropyl, cyclobutyl, cyclopentyl and cyclohexyl.

The term substituted cycloalkyl refers to cycloalkyl moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as C$_1$-C$_6$ alkoxy), substituted alkoxy, aryloxy (such as phenoxy), nitro, mercapto, carboxyl, oxo, carbamoyl, alkyl, substituted alkyls such as trifluoromethyl, aryl, substituted aryls, heterocyclyl, heteroaryl, alkylsulfonyl, arylsulfonyl and —OCF$_3$. When the specification and especially the claims refer to a particular substuituent for a cycloalkyl, that substituent can potentially occupy one or more of the substitutable positions on the cycloalkyl. For example, reciting that a cycloalkyl has a fluoro substituent, would embrace mono-, di-, and a higher degree of substitution on the cycloalkyl moiety. Examples of cycloalkyls include cyclopropy, cyclobutyl, cyclopentyl, cyclohexyl, tetrahydronaphthyl and indanyl.

"Aryl" when used alone or as part of another term means an aromatic carbocyclic group whether or not fused having the number of carbon atoms designated, or if no number is designated, from 6 up to 14 carbon atoms. Particular aryl groups include phenyl, naphthyl, biphenyl, phenanthrenyl, naphthacenyl, indolyl, and the like (see e.g., Lange's Handbook of Chemistry (Dean, J. A., ed) 13$^{th}$ ed. Table 7-2 [1985].

The term substituted aryl refers to aryl moieties having substituents replacing one or more hydrogens on one or more (usually no more than six) carbon atoms of the aromatic hydrocarbon core. Such substituents are independently selected from the group consisting of: halo (e.g., I, Br, Cl, F), hydroxy, amino, cyano, alkoxy (such as C$_1$-C$_6$ alkoxy and particularly lower alkoxy), substituted alkoxy, aryloxy (such as phenoxy), nitro, mercapto, carboxyl, carbamoyl, alkyl, substituted alkyl (such as trifluoromethyl), aryl, —OCF$_3$, alkylsulfonyl (including lower alkyl sulfonyl), aryl sulfonyl, heterocyclyl and heteroaryl. Examples of such substituted phenyls include but are not limited to a mono- or di(halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl; 3-fluorophenyl, 4-fluorophenyl, a mono- or di(hydroxy) phenyl group such as 4-hydroxyphenyl, 3-hydroxyphenyl, 2,4-dihydroxyphenyl, the protected-hydroxy derivatives thereof; a nitrophenyl group such as 3- or 4-nitrophenyl; a cyanophenyl group, for example, 4-cyanophenyl; a mono- or di(lower alkyl) phenyl group such as 4-methylphenyl, 2,4-dimethylphenyl, 2-methylphenyl, 4-(iso-propyl) phenyl, 4-ethylphenyl, 3-(n-propyl)phenyl; a mono or di(alkoxy) phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl,4-(t-butoxy)phenyl, 3-ethoxy-4-methoxyphenyl; 3- or 4-trifluoromethylphenyl; a mono- or dicarboxyphenyl or (protected carboxy) phenyl group such 4-carboxyphenyl; a mono- or di(hydroxymethyl) phenyl or (protected hydroxymethyl) phenyl such as 3-(protected hydroxymethyl) phenyl or 3,4-di(hydroxymethyl)phenyl; a mono- or di(aminomethyl) phenyl or (protected aminomethyl) phenyl such as 2-(aminomethyl)phenyl or 2,4-(protected aminomethyl)phenyl; or a mono- or di(N-(methylsulfonylamino)) phenyl such as 3-(N-methylsulfonylamino) phenyl. Also, the substituents, such as in a disubstituted phenyl groups, can be the same or different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, as well as for tri-substituted phenyl groups where the substituents are different, as for example 3-methoxy-4-benzyloxy-6-methyl sulfonylamino, 3-methoxy-4-benzyloxy-6-phenyl sulfonylamino, and tetra-substituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. When the specification and especially the claims refer to a particular substituent for an aryl, that substituent can potentially occupy one or more of the substitutable positions on the aryl. For example, reciting that an aryl has a fluoro substituent, would embrace mono-, di-, tri, tetra and a higher degree of substitution on the aryl moiety. Fused aryl rings may also be substituted with the substituents specified herein, for example with 1, 2 or 3 substituents, in the same manner as substituted alkyl groups. The terms aryl and substituted aryl do not include moieties in which an aromatic ring is fused to a saturated or partially unsaturated aliphatic ring.

"Heterocyclic group", "heterocyclic", "heterocycle", "heterocyclyl", "heterocycloalkyl" or "heterocyclo" alone and when used as a moiety in a complex group, are used interchangeably and refer to any mono-, bi-, or tricyclic, saturated or unsaturated, non-aromatic hetero-atom-containing ring system having the number of atoms designated, or if no number is specifically designated then from 5 to about 14 atoms, where the ring atoms are carbon and at least one heteroatom and usually not more than four heteroatoms (i.e., nitrogen, sulfur or oxygen). Included in the definition are any bicyclic groups where any of the above heterocyclic rings are fused to an aromatic ring (i.e., an aryl (e.g., benzene) or a heteroaryl ring). In a particular embodiment the group incorporates 1 to 4 heteroatoms. Typically, a 5-membered ring has 0 to 1 double bonds and a 6- or 7-membered ring has 0 to 2 double bonds and the nitrogen or sulfur heteroatoms may optionally be oxidized (e.g., SO, $SO_2$), and any nitrogen heteroatom may optionally be quaternized. Particular unsubstituted non-aromatic heterocycles include morpholinyl (morpholino), pyrrolidinyls, oxiranyl, indolinyls, 2,3-dihydoindolyl, isoindolinyls, 2,3-dihydoisoindolyl, tetrahydroquinolinyls, tetrahydroisoquinolinyls, oxetanyl, tetrahydrofuranyls, 2,3-dihydrofuranyl, 2H-pyranyls, tetrahydropyranyls, aziridinyls, azetidinyls, 1-methyl-2-pyrrolyl, piperazinyls and piperidinyls.

The term substituted heterocyclo refers to heterocyclo moieties having substituents replacing one or more hydrogens on one or more (usually no more than six) atoms of the heterocyclo backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, carboxyl, oxo, carbamoyl, alkyl, substituted alkyl (such as trifluoromethyl), —$OCF_3$, aryl, substituted aryl, alkylsulfonyl (including lower alkylsulfonyl), and arylsulfonyl. When the specification and especially the claims refer to a particular substituent for a heterocycloalkyl, that substituent can potentially occupy one or more of the substitutable positions on the heterocycloalkyl. For example, reciting that a heterocycloalkyl has a fluoro substituent, would embrace mono-, di-, tri, tetra and a higher degree of substitution on the heterocycloalkyl moiety.

"Heteroaryl" alone and when used as a moiety in a complex group refers to any mono-, bi-, or tricyclic aromatic ring system having the number of atoms designated, or if no number is specifically designated then at least one ring is a 5-, 6- or 7-membered ring and the total number of atoms is from 5 to about 14 and containing from one to four heteroatoms selected from the group consisting of nitrogen, oxygen, and sulfur (Lange's Handbook of Chemistry, supra). Included in the definition are any bicyclic groups where any of the above heteroaryl rings are fused to a benzene ring. The following ring systems are examples of the heteroaryl groups denoted by the term "heteroaryl": thienyls (alternatively called thiophenyl), furyls, imidazolyls, pyrazolyls, thiazolyls, isothiazolyls, oxazolyls, isoxazolyls, triazolyls, thiadiazolyls, oxadiazolyls, tetrazolyls, thiatriazolyls, oxatriazolyls, pyridyls, pyrimidinyls (e.g., pyrimidin-2-yl), pyrazinyls, pyridazinyls, thiazinyls, oxazinyls, triazinyls, thiadiazinyls, oxadiazinyls, dithiazinyls, dioxazinyls, oxathiazinyls, tetrazinyls, thiatriazinyls, oxatriazinyls, dithiadiazinyls, imidazolinyls, dihydropyrimidyls, tetrahydropyrimidyls, tetrazolo [1, 5-b] pyridazinyl and purinyls, as well as benzo-fused derivatives, for example benzoxazolyls, benzofuryls, benzothienyls, benzothiazolyls, benzothiadiazolyl, benzotriazolyls, benzoimidazolyls, isoindolyls, indazolyls, indolizinyls, indolyls, naphthyridines, pyridopyrimidines, phthalazinyls, quinolyls, isoquinolyls and quinazolinyls.

The term substituted heteroaryl refers to heteroaryl moieties (such as those identified above) having substituents replacing one or more hydrogens on one or more (usually no more than six) atoms of the heteroaryl backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, carbamoyl, alkyl, substituted alkyl (such as trifluoromethyl), —$OCF_3$, aryl, substituted aryl, alkylsulfonyl (including lower alkylsulfonyl), and arylsulfonyl. When the specification and especially the claims refer to a particular substituuent for a heteroaryl, that substituent can potentially occupy one or more of the substitutable positions on the heteroaryl. For example, reciting that a heteroaryl has a fluoro substituent, would embrace mono-, di-, tri, tetra and a higher degree of substitution on the heteroaryl moiety.

Particular "heteroaryls" (including "substituted heteroaryls") include; 1H-pyrrolo[2,3-b]pyridine, 1,3-thiazol-2-yl, 4-(carboxymethyl)-5-methyl-1,3-thiazol-2-yl, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl, 1,3-oxazol-2-yl, 1,3, 4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(methylsulfonic acid)-1H-tetrazol-5-yl, 2-methyl-1H-tetrazol-5-yl, 1,2,3-triazol-5-yl, 1-methyl-1,2, 3-triazol-5-yl, 2-methyl-1, 2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetra-hydro-5,6-dioxo-4-methyl-as-triazin-3-yl, 1,4,5,6-tetra-hydro-4-(formylmethyl)-5,6-dioxo-as-triazin-3-yl, 2,5-di-hydro-5-oxo-6-hydroxy-astriazin-3-yl, 2,5-dihydro-5-oxo-6-hydroxy-as-triazin-3-yl, 2,5-dihydro-5-oxo-6-hydroxy-2-methyl-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2, 6-dimethyl-as-triazin-3-yl, tetrazolo [1,5-b]pyridazin-6-yl, 8-aminotetrazolo [1,5-b]-pyridazin-6-yl, quinol-2-yl, quinol-3-yl, quinol-4-yl, quinol-5-yl, quinol-6-yl, quinol-8-yl, 2-methyl-quinol-4-yl, 6-fluoro-quinol-4-yl, 2-methyl, 8-fluoro-quinol-4-yl, isoquinol-5-yl, isoquinol-8-yl, isoquinol-1-yl, and quinazolin-4-yl. An alternative group of "heteroaryl" includes: 5-methyl-2-phenyl-2H-pyrazol-3-yl, 4-(carboxymethyl)-5-methyl-1,3-thiazol-2-yl, 1,3,4-tri-azol-5-yl, 2-methyl-1,3,4-triazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl, 2,5-dihydro-5-oxo-6-hydroxy-2-methyl-as-triazin-3-yl, tet-razolo [1,5-b]pyridazin-6-yl, and 8-aminotetrazolo [1,5-b] pyridazin-6-yl.

L is a linking group or a bond covalently linking one monomer, [P1-P2-P3-P4] to the other monomer, [P1'-P2'-P3'-P4']. Commonly, -L- links P2 to P2' position such as at R3 or P4 to P4' such as at M, G, Q, or $R^7$, or both P2 to P2' and P4 to P4'. L, therefore, can be a single or double covalent bond or a contiguous chain, branched or unbranched, sub-stituted or unsubstituted, of 1 to about 100 atoms, typically 1 to about 30 atoms, e.g., an optionally substituted alkylene, alkenylene, alkylyne, cycloalkyl, alkylcycloalkyl, alkylary-lalkyl chain of 2 to 20 atoms optionally with 1-4 heteroatoms selected from —O—, —NH—, and —S—. Illustrative examples of L are a single or double covalent bond, C1-12 alkylene, substituted C1-12 alkylene, C1-12 alkenylene, substituted C1-12 alkenylene, C1-12 alkynylene, substituted C1-12 alkynylene, $X_n$-phenyl-$Y_n$, or $X_n$-(phenyl)$_2$-$Y_n$, wherein X and Y are independently C1-6 alkylene, substi-tuted C1-6 alkylene, C1-6 alkenylene, substituted C1-6 alkenylene, C1-6 alkynylene, substituted C1-6 alkynylene, or S(O)$_2$.

Illustrative P3/P3' groups include, without limitation:

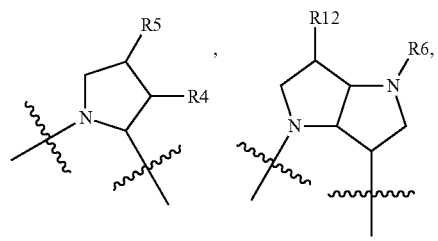

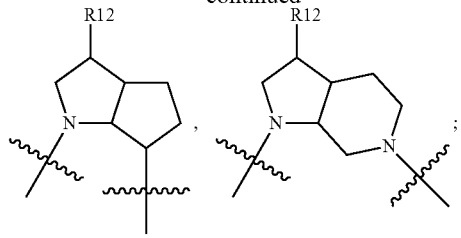

wherein $R^6$ is —H, C1-6 alkyl, substituted C1-6 alkyl, C1-6 alkoxy, substituted C1-6 alkoxy, C1-6 alkyl sulfonyl, aryl sulfonyl, cycloalkyl, substituted cycloalkyl, heterocy-cloalkyl, substituted heterocycloalkyl, aryl, substituted aryl, heteroaryl, or substituted heteroaryl; $R^4$, $R^5$, and $R^{12}$ are, independently, —H, —OH, C1-6 alkyl, C1-6 heteroalkyl, C1-6 alkoxy, aryloxy, cycloalkyl, heterocycloalkyl, aryl, C1-6 alkyl aryl, or heteroaryl, or C1-6 alkyl heteroaryl, optionally substituted in each case except when $R^4$ is —H or —OH.

As mentioned, in certain illustrative embodiments, the Smac mimetic used in the practice of the invention is bivalent.

In certain illustrative embodiments, a selected Smac mimetic derepresses XIAP-mediated caspase-3 repression and/or degrades cIAP-1 not bound to TRAF2 (non TRAF2-bound, e.g., "cytoplasmic" cIAP-1 or "free" cIAP-1) as well as cIAP1 bound to TRAF2 and/or degrades cIAP-2 bound to TRAF2 but does not degrade cIAP-2 not bound to TRAF2 or weakly degrades cIAP-2 not bound to TRAF2 relative to degradation of cIAP-2 bound to TRAF2.

Smac mimetics used in the practice of the current inven-tion can cause degradation of cIAP-2 not bound to TRAF2, but the extent of such degradation on a percentage basis will be less than the extent of degradation of TRAF2-bound cIAP-2. The significance of the difference in effects of a Smac mimetic on the cIAP-2 not bound to TRAF2, has been observed to correlate with the tolerability (or safety profile) of a Smac mimetic in animals. If a first Smac mimetic causes less degradation of cIAP-2 not bound to TRAF2, relative to degradation of TRAF2-bound cIAP-2, than a second Smac mimetic, i.e., a structurally different Smac mimetic, then the first Smac mimetic is likely to be better tolerated in (i.e., more safely administered to) animals. More specifically, a skilled person can select two Smac mimetics, each causing degradation of cIAP-1 not bound to TRAF2, TRAF2-bound cIAP-1 and TRAF2-bound cIAP-2 with one exhibiting a different (lesser) degree of degradation of cIAP-2 not bound to TRAF2, then the compound that causes less degradation of cIAP-2 not bound to TRAF2, is likely to be better tolerated with no significant loss in antitumor potency.

The degradation kinetics of non-TRAF2-bound cIAP-1, non-TRAF2-bound cIAP-2, TRAF2-bound cIAP-1 and TRAF2-bound cIAP-2 can be measured by western analysis. The extent of degradation can be observed visually in such assays over a period of time. For example, the extent of degradation of non-TRAF2-bound cIAP-2 and TRAF2-bound cIAP-2 may appear to be substantially the same immediately following treatment of cells with a Smac mimetic but after several minutes, e.g., after 15 to 30 minutes, increased degradation of TRAF2-bound cIAP-2 relative to degradation of non-TRAF2-bound cIAP-2 may be observed in treated cells. Differences in extent of degrada-tion can also be quantified. For example, in the case of western analysis using green fluorescence protein tagged cIAPs, the extent of degradation can be quantified using a device that measures the intensity of fluorescence.

For a Smac mimetic that is likely to be better tolerated in animals, the extent of degradation of non-TRAF2-bound cIAP-2 will generally be less than 75% of (or about 75% of), i.e., about 75% or less than, the extent of degradation of TRAF2-bound cIAP-2 at relevant concentrations, for at least about 15 minutes, e.g., 30 to 120 minutes (or about 30 to about 120 minutes). The amount of Smac mimetic used in such assay will vary with the potency of the Smac mimetic but will generally be less than 1 uM, such as e.g., between about 1 and about 500 nM or between about 10 and about 150 nM In some cases, the extent of degradation of non-TRAF2-bound cIAP-2 will be less than 50% of (or about 50% of), i.e., about 50% or less than; or less than 25% of (or about 25% of), i.e., about 25% or less than; or less than 10% of (or about 10% of), i.e., about 10% or less than, the extent of the degradation of TRAF2-bound cIAP-2. For example, in a cIAP degradation assay with a Smac mimetic having a cIAP degradation profile of the invention, TRAF2-bound cIAP-2 may be about 70-75% degraded after 30 minutes (i.e., only about 30% of the originally detected amount of TRAF2-bound cIAP-2 is still detectable); whereas non-TRAF2-bound cIAP-2 may only be about 35-40% degraded (i.e., 60% to 65% of the originally detected amount of non-TRAF2-bound cIAP-2 is still detectable) after 30 minutes. In this case, the Smac mimetic is said to degrade non-TRAF2-bound cIAP-2 at about 50% or less than the extent of degradation of TRAF2-bound cIAP-2 (35% to 40% divided by (70% to 75%)=about 50%).

The induction of apoptosis is highly specific for susceptible tumours, whereas normal tissue appears to be spared. For instance, certain Smac mimetics are capable of killing tumour cells in vitro in the picomolar concentration range, while having no effect on non-tumour cells in the 100 micromolar range.

Several Smac mimetics have been developed that have significant anti-tumour activity in preclinical studies. Of those that have entered the clinic, birinapant (TL32711) is a potent bivalent small molecule Smac mimetic. Birinapant is identified as Compound 15 in U.S. Pat. No. 8,283,372. In an embodiment, the IAP antagonist is birinapant.

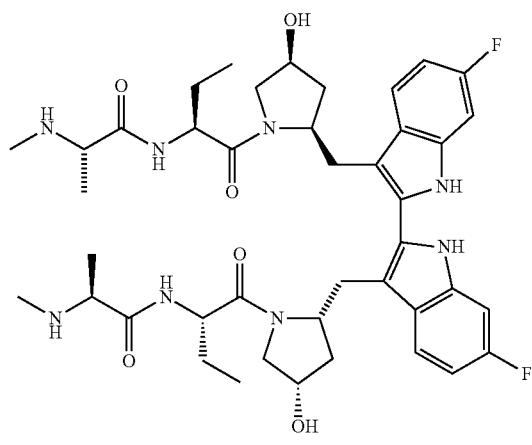

birinapant (TL32711)

Additional information regarding the activity of birinapant and similar compounds is provided in U.S. Ser. No. 14/246,956, the disclosure of which is incorporated herein by reference.

Pharmaceutical compositions of Smac mimetics may comprise a therapeutically effective amount of a compound as described above, or a pharmaceutically acceptable salt or other form thereof together with one or more pharmaceutically acceptable excipients. The phrase "pharmaceutical composition" refers to a composition suitable for administration in medical or veterinary use. The composition may also comprises additional active agents. For example the composition may include cytokines such as TNF-α or small molecule inhibitors or antibiotics. It should be appreciated that the determinations of proper dosage forms, dosage amounts, and routes of administration for a particular patient are within the level of ordinary skill in the pharmaceutical and medical arts.

Compositions suitable for parenteral administration conveniently comprise a sterile aqueous preparation of a compound or composition of the invention, which is preferably isotonic with the blood of the recipient. This aqueous preparation may be formulated according to known methods using suitable dispersing or wetting agents, emulsifying and suspending agents. Various antibacterial and antifungal agents, for example, parabens, chlorobutanol, phenol, and sorbic acid also may be included. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Prolonged absorption of the injectable pharmaceutical form can be brought about by the use of agents delaying absorption, for example, aluminum monostearate and gelatin. Carrier formulation suitable for subcutaneous, intravenous, intramuscular, etc. administrations can be found in Remington's Pharmaceutical Sciences, Mack Publishing Co., Easton, Pa. which is incorporated herein in its entirety by reference thereto.

A pharmaceutical composition in intravenous unit dose form may comprise, e.g., a vial or pre-filled syringe, or an infusion bag or device, each comprising an effective amount or a convenient fraction of an effective amount such that the contents of one vial or syringe are administered at a time.

Administration can be repeated up to about 4 times per day over a period of time, if necessary to achieve a cumulative effective dose, e.g., a cumulative dose effective to produce control of infection. A dosing regimen can be, e.g., daily or twice-weekly intravenous or subcutaneous injections or oral or topical delivery, or, e.g., once weekly doses in cycles of three weeks on and one week off, or continuous, for as long as the treatment is effective, e.g., until infection is controlled or the drug is not tolerated. The effective dose administered in each injection is an amount that is effective and tolerated.

An effective dose is one that over the course of therapy, which may be, e.g., 1 or more weeks, results in treatment of the disorder, i.e., a decrease in the rate of disease progression, termination of disease.

Solid dosage forms for oral administration include capsules, tablets, pills, powders, and granules. In such solid dosage forms, the compound is admixed with at least one inert pharmaceutically acceptable excipient such as (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid dosage forms such as tablets, dragees, capsules, pills, and granules also can be prepared with coatings and shells, such as enteric coatings and others well known in the art. The solid dosage form also may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients. Such solid dosage forms may generally contain from 1% to 95% (w/w) of the active compound. In certain embodiments, the active compound ranges from 5% to 70% (w/w).

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: one contains the Smac mimetic used in the method of the present invention, and a second one contains a second active pharmaceutical ingredient. The kit comprises a container for containing the separate compositions such as a divided bottle or a divided foil packet. Additional examples of containers include syringes, e.g., pre-filled syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a substance of the present invention can consist of one tablet or capsule, while a daily dose of the second substance can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Liquid dosage forms for oral administration include pharmaceutically acceptable emulsions, solutions, suspensions, syrups, and elixirs. In addition to the compound or composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances. Besides such inert diluents, the composition can also include adjuvants, such as wetting agents, emulsifying and suspending agents, sweetening, flavoring, and perfuming agents.

The compounds and compositions used in the method of the present invention also may benefit from a variety of delivery systems, including time-released, delayed release or sustained release delivery systems. Such option may be particularly beneficial when the compounds and composition are used in conjunction with other treatment protocols as described in more detail below.

Many types of controlled release delivery systems are available and known to those of ordinary skill in the art. They include polymer base systems such as poly(lactideglycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, as used herein, means that the implant is constructed and arranged to deliver therapeutic levels of the active compound for at least 30 days, and preferably 60 days. Long-term sustained release implants are well-known to those of ordinary skill in the art and include some of the release systems described above.

IAP antagonists also include molecules that reduce the expression of an IAP gene, such as cIAP1 or cIAP2. Suitable antagonists that are capable of reducing the expression of an IAP gene would be known to persons skilled in the art. Examples include nucleic acid molecules, such as RNA or DNA molecules (including double-stranded or single-stranded), and peptides, such as antisense peptide nucleic acids, that interfere with the expression of the target gene.

Useful DNA molecules include antisense, as well as sense (e.g. coding and/or regulatory) DNA molecules. Antisense DNA molecules include short oligonucleotides. Persons skilled in the art would be able to design suitable short oligonucleotides for use in accordance with the present invention. An example is the XIAP antisense oligonucleotide, AEG35156, as described by Carter et al. (*Apoptosis*, 2011 Vol. 16(1):67-74). Other examples of useful DNA molecules include those encoding interfering RNAs, such as shRNA and siRNA. Yet another example are catalytic DNA molecules known as DNAzymes.

Useful RNA molecules capable of reducing the expression of an IAP gene, also referred to herein as RNA interference molecules, include siRNA, dsRNA, stRNA, shRNA, and miRNA (e.g., short temporal RNAs and small modulatory RNAs) and ribozymes.

RNA interference (RNAi) is particularly useful for specifically inhibiting the production of a particular protein. Although not wishing to be limited by theory, Waterhouse et al. (1998) have provided a model for the mechanism by which dsRNA can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998, *Proc Natl Acad Sci USA*. 95(23):13959-64), Smith et al. (2000, *Nature*. 407:319-320), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from the cell that destroys both the double stranded RNA and also the homologous RNA transcript from the target gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the cell in which it is to be introduced, e.g., as determined by standard BLAST search.

Synthesis of RNAi molecules suitable for use with present invention can be effected by first scanning the mRNA sequence of the target downstream of the AUG start codon for AA dinucleotide sequences. Occurrence of each AA and the 3' adjacent 19 nucleotides is recorded as potential siRNA target sites. Preferably, siRNA target sites are selected from the open reading frame. Second, potential target sites are compared to an appropriate genomic database using any sequence alignment software, such as BLAST. Putative target sites which exhibit significant homology to other coding sequences are filtered out. Qualifying target sequences are selected as template for SiRNA synthesis. Preferred sequences are those including low G/C content as these have proven to be more effective in mediating gene silencing as compared to those with G/C content higher than 55%. Several target sites are preferably selected along the length of the target gene for evaluation.

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005, Funct Integr Genomics, 5(3):129-35; Pasquinelli et al., 2005, Curr Opin Genet Dev. 15(2):200-5; Almeida and Allshire, 2005, TRENDS Cell Biol, 15(5):251-8).

DNAzymes are single-stranded polynucleotides which are capable of cleaving single and double stranded polynucleotides which are capable of cleaving both single and double stranded target sequences (Breaker and Joyce. Chemistry and Biology 1995; 2:655; Santoro and Joyce. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro and Joyce. supra; for rev of DNAzymes, see Khachigian, Curr Opin Mol Ther 4:119-21; 2002).

Examples of construction and amplification of synthetic, engineered DNAzymes recognizing single and double-stranded target cleavage sites have been disclosed in U.S. Pat. No. 6,326,174 to Joyce et al.

The terms "double stranded RNA" or "dsRNA" refer to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA, comprises a dsRNA molecule.

Other suitable RNA interference molecules include unmodified and modified double stranded (ds) RNA molecules including, short-temporal RNA (stRNA), small interfering RNA (siRNA), short-hairpin RNA (shRNA), microRNA (miRNA) and double-stranded RNA (dsRNA). The dsRNA molecules (e.g. siRNA) also may contain 3' overhangs, such as 3'UU or 3'TT overhangs.

In an embodiment, the siRNA molecules of the present invention have a double stranded structure. In an embodiment, the siRNA molecules of the present invention are double stranded for more than about 25%, more than about 50%, more than about 60%, more than about 70%, more than about 80%, more than about 90% of their length.

As used herein, "gene silencing" induced by RNA interference refers to a decrease in the mRNA level in a cell for a target gene (e.g., cIAP1 gene and/or cIAP2 gene) by at least about 5%, about 10%, about 20%, about 30%, about 40%, about 50%, about 60%, about 70%, about 80%, about 90%, about 95%, about 99%, about 100% of the mRNA level found in the cell in the absence of RNA interference.

The RNA interference molecules also include modified RNA molecules having one or more non-natural nucleotides; that is, nucleotides other than adenine "A", guanine "G", uracil "U", or cytosine "C". A modified nucleotide residue or a derivative or analog of a natural nucleotide may also be used. Any modified residue, derivative or analog may be used to the extent that it does not eliminate or substantially reduce (by at least 50%) RNAi activity of the molecule. Examples of suitable modified residues include aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NE12 UTP, 2'NE12 CTP, and 2'F. UTP. Suitable modified nucleotides also include aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH2 uridine, 2'NE12 cytidine, and 2'F uridine, including the free pho (NTP) RNA molecules, as well as all other useful forms of the nucleotides.

RNA interference molecules may also contain modifications in the ribose sugars, as well as modifications in the phosphate backbone of the nucleotide chain. For example, siRNA or miRNA molecules containing α-D-arabinofuranosyl structures in place of the naturally-occurring α-D-ribonucleosides found in RNA can be used as RNA interference molecules according to the present invention. Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly α-arabinose. Phosphorothioate linkages can also be used to stabilize the siRNA and miRNA molecules.

An "siRNA" refers to a nucleic acid that forms a double stranded RNA, which double stranded RNA has the ability to reduce or inhibit expression of a gene or target gene when the siRNA is expressed in the same cell as the gene or target gene. "siRNA" thus refers to the double stranded RNA formed by the complementary strands. The complementary portions of the siRNA that hybridize to form the double stranded molecule typically have substantial or complete identity. In an embodiment, an siRNA refers to a nucleic acid that has substantial or complete identity to a target gene and forms a double stranded siRNA. The sequence of the siRNA can correspond to the full length target gene, or a subsequence thereof.

In an embodiment, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

Suitable siRNAs also include small hairpin (also called stem loop) RNAs (shRNAs). In an embodiment, the shRNA comprises short, e.g. about 19 to about 25 nucleotide, antisense strand, followed by a nucleotide loop of about 5 to about 9 nucleotides, and the analogous sense strand. Alternatively, the sense strand may precede the nucleotide loop structure and the antisense strand may follow.

In an embodiment, the antagonist of IAP is siRNA, shRNA or miRNA.

Specific RNA interference molecules, such as siRNA, shRNA and miRNA molecules, can be easily designed by one skilled in the art having regard to the sequence of the target gene.

In an embodiment, the siRNA, shRNA or miRNA is targeted against a sequence selected from the group consisting of NCBI Reference Sequence: NM_001166.4, NCBI Reference Sequence: NM_001256163.1, NCBI Reference Sequence: NM_001256166.1, GenBank: DQ068066.1, NCBI Reference Sequence: NM_001165.4, NCBI Reference Sequence: NM_182962.2, GenBank: BCO37420.1, NCBI Reference Sequence: NM_001167.3, NCBI Reference Sequence: NM_001204401.1, NCBI Reference Sequence: NR_037916.1, and NCBI Reference Sequence: NG_007264.1.

Other RNA molecules which are single stranded, or are not considered to be RNA interference molecules, may also be useful as therapeutic agents in accordance with the present invention, including messenger RNAs (and the progenitor pre-messenger RNAs), small nuclear RNAs, small nucleolar RNAs, transfer RNAs and ribosomal RNAs.

IAP antagonists capable of reducing the expression of an IAP gene, as herein described (e.g., RNA interference molecules such as siRNA, dsRNA, stRNA, shRNA, and miRNA), can be administered to the subject in need thereof by any suitable means and route of administration, as would be known to persons skilled in the art (e.g., gene therapy or gene delivery methods). It would be understood that the IAP antagonist is to be administered to a subject in such a way as to ensure that the antagonist is able to contact and enter a cell in the subject, whether the cell is infected with the pathogen or is at least capable of becoming infected with the pathogen. Examples of suitable routes of administration include intravenous, intramuscular, topical, oral, intranasal or by gene gun or hypospray instrumentation.

Alternatively, the method of treatment may involve contacting a cell derived from the subject ex vivo or in vitro with the IAP antagonist and under conditions that will facilitate entry of the IAP antagonist into the cell (i.e., transfection). Standard transfection techniques are known to persons skilled in the art. In an embodiment, the IAP antagonist is brought into contact with an autologous cell from the subject and under conditions that favour entry of the IAP antagonist into the cell and its subsequent transfection, such that the IAP antagonist is capable of blocking or at least partially inhibiting the expression of the IAP gene in the transfected cell. The transfected cell is then administered to the subject, where it will be at least partially resistant to infection. The type of cell that is selected for transfection in vitro or ex vivo is preferably a cell that is at least capable of becoming infected by a pathogen. The type of cell that is selected for transfection in vitro or ex vivo may therefore depend on the type of infection that is to be treated in a subject. For example, where the infectious pathogen is HIV, the autologous cell may be a T lymphocyte. Other cell types that may be suitable for transfection in vitro or ex vivo in accordance with the present invention include macrophages, fibroblasts, monocytes, neutrophils, B lymphocytes, stem cells (e.g., somatic stem cells) and progenitor cells. Examples of progenitor cells that can be transfected in accordance with the methods of the present invention include precursors of erythrocytes and hematopoietic stem cells.

The method of the present invention can also be used to treat intracellular infection by other pathogens. For example, an imperative for *Mycobacterium tuberculosis* is the establishment of latency in the host cell, which is a highly complex endeavor for an intracellular bacterium that resides in macrophages. Consequently, *Mycobacterium tuberculosis* must critically disable all cell death signalling[4-6] to allow its continued persistence in macrophages[10-13]. *Mycobacterium tuberculosis* infected macrophages are under substantial cellular stress that should induce apoptosis[14]. Through poorly understood mechanisms, the cell death programs that should ensure the demise of an infected cell and its resident microbe, are antagonized by this pathogen[14]. The inventors have shown data that strongly support the notion that promotion of programmed cell death in cells infected with *Mycobacterium tuberculosis* would assist with the clearance of the pathogen. Similarly, to enable a productive lifecycle and to promote latency, HIV in some cells and at some point, must antagonize host cell death[15-19]. Host cell death can be a consequence of sensing microbial infection or through the effects of death inducing molecules liberated by immune cells. Intracellular pathogens antagonize these responses to facilitate their persistence and dissemination[4-6]. Interfering with IAPB is a mechanism that can be used to resensitize infected cells to cell death inducing factors and pathways that promote clearance of pathogens.

In an embodiment, infection is caused by a virus, bacterium, fungus, yeast or protozoa.

In an embodiment, the infection is caused by a virus selected from the group consisting of Human papillomaviruses, Herpes viruses including herpes simplex 1/2, varicella zoster, EBV, CMV, HHV-6/7, HTLV, Human papovaviruses, including JC virus and BK virus, adeno and parvoviruses, HIV, HBV and HCV.

In an embodiment, the infection is caused by a bacterium selected from the group consisting of *Salmonella* spp., *Ehrlichia* spp., *Mycobacteria* spp., *Spirochetes*, *Legionella* spp., *Listeria* spp., *Rickettsia* spp., *Chlamydia* spp., *Mycoplasma* spp., *Coxiella* spp., *Yersinia* spp., *Francisella* spp., *Brucella* spp., *Neisseria* spp, and *Nocardia* spp.

In an embodiment, the infection is caused by a fungus or yeast selected from the group consisting of *Histoplasma* spp., *Aspergillus* spp., *Cryptococcus* spp., and *Pneunocystis jirovecii*.

In an embodiment, the infection is caused by protozoa selected from the group consisting of Trypanosomatids (e.g., *Leishmania* spp.), Apicomplexans, including liver forms of *Plasmodium* spp., *Toxoplasma* spp., and *Cryptosporidium* spp.

The present invention also provides use of an IAP antagonist for the treatment of an intracellular infection in a subject.

The method of the present invention may further comprise the administration of one or more additional therapeutic agents. Persons skilled in the art would understand that the type of additional therapeutic agent(s) will depend on the infection to be treated. For example, where the infection is a viral infection such as an HBV infection, the subject may be further administered with an nucleoside analogue antiviral agent. Examples of such agents include Nucleoside analogue drugs include Didanosine, Vidarabine, Cytarabine, Emtricitabine, Lamivudine, Zalcitabine, Abacavir, Aciclovir, Entecavir, Stavudine, Telbivudine, Zidovudine (azidothymidine, or AZT) and Idoxuridine. Preferred agents are selected from the group consisting of lamivudine, adefovir, tenofovir, telbivudine and entecavir. Where the infection is an HCV infection, the subject may be further administered with pegylated IFN α and ribavirin, and/or Miravirsen (Janssen et al. N Engl J Med, 2013, vol. 368(18):1685-94).

Another preferred additional therapeutic agent is TRAIL. Additional information regarding TRAIL may be found in WO 97/01633, WO 02/085946, WO 02/22175 and WO 2009/025743. The disclosure of each of these documents is included herein by reference.

The additional therapeutic agent(s) may be administered simultaneously (e.g., in the same formulation as the IAP antagonist) or sequentially; that is, either before or after administration of the IAP antagonist. For sequential administration, the additional therapeutic agent(s) may be administered within seconds, minutes, hours, days or weeks of the IAP antagonist.

The IAP antagonist can be delivered to a subject in need thereof by any suitable means known to persons skilled in the art. For example, persons skilled in the art would understand that, where the IAP antagonist is an RNA interference molecule, the method of administration would need to facilitate the delivery of the IAP antagonist to the cell cytoplasm where it can interact with the target sequence. Where the IAP antagonist is an siRNA molecule, the RNA interference molecule may be delivered to a subject by the co-administration of a hepatocyte-targeted, N-acetylgalactosamine-conjugated melittin-like peptide (NAG-MLP) with a liver-tropic cholesterol-conjugated siRNA (see, e.g., Woodell et al., *Molecular Therapy*, 2013 May; 21(5): 973-985) Where the molecule is an antisense DNA oligonucleotide molecule, it may be delivered to a subject in need thereof by the method described by Janssen et al. (*N Engl J Med*, 2013, vol. 368(18):1685-94).

In an alternative embodiment gene therapy may be conducted on the subject to decrease the expression of or inactivate one or more IAP genes in the subject.

The method of delivery includes the use of solutions and suspensions that are administrable to the subject. Suitable modes of administration would be known to persons skilled in the art. Examples include intravenous, subcutaneous, intramuscular or intraperitoneal.

The subject in which a infection is to be treated may be a human or a mammal of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), horses, and birds including those kinds of birds that are endangered, kept in zoos, and fowl, and more particularly domesticated fowl, e.g., poultry, such as turkeys, chickens, ducks, geese, guinea fowl, and the like, as they are also of economical importance to humans. The term "subject" does not denote a particular age. Thus, both adult and newborn subjects are intended to be covered.

The present invention also provides use of an IAP antagonist in the manufacture of a medicament for the treatment of an intracellular infection in a subject.

The medicament may include further amounts of pharmaceutically acceptable and suitable carriers, diluents, or excipients. These include all known solvents, dispersion media, fillers, solid carriers, castings, antifungal and antibacterial agents, surfactants, isotonic and absorption agents and the like. It will be understood that the medicament may also include one or more additional therapeutic agents (i.e., in addition to the IAP antagonist), as herein described. For example, where the infection is an HBV infection, the medicament may further comprise an HBV anti-viral agent selected from the group consisting of lamivudine, adefovir, tenofovir, telbivudine and entecavir. Where the infection is an HCV infection, the medicament may further comprise pegylated IFN α and ribavirin, and/or Miravirsen (Janssen et al. *N Engl J Med*, 2013, vol. 368(18):1685-94).

The present invention also contemplates co-formulation and/or co-administration with other pharmaceutically active agents including, without limitation, TNF-α agonists such as TNF-α, TRAIL (TNF-related apoptosis inducing ligand) or TRAIL agonists such as but not limited to TRAIL receptor antibodies.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

EXAMPLES

Example 1

Hepatitis B Infection of Mice

The present inventors adapted a technique[7,8] that can be used to cause HBV infection in mice. Naked plasmid DNA containing greater than genome length HBV1.2 flanked by the inverted terminal repeats of adeno-associated virus is injected hydrodynamically to cause substantial inferior vena caval pressures to force DNA into the liver where it is incorporated into hepatocytes[7,8]. Importantly, the DNA injected into animals does not contain any adeno-associated viral coding sequences. The plasmid is not encapsulated so there are no viral structural or non-structural proteins in the injected preparation.

Mice were bled intermittently and their serum was isolated. Qiagen viral DNA extraction kit was used to purify viral DNA. Absolute quantification of HBV genome was achieved by RT-PCR, as described previously[9].

Figure 2:
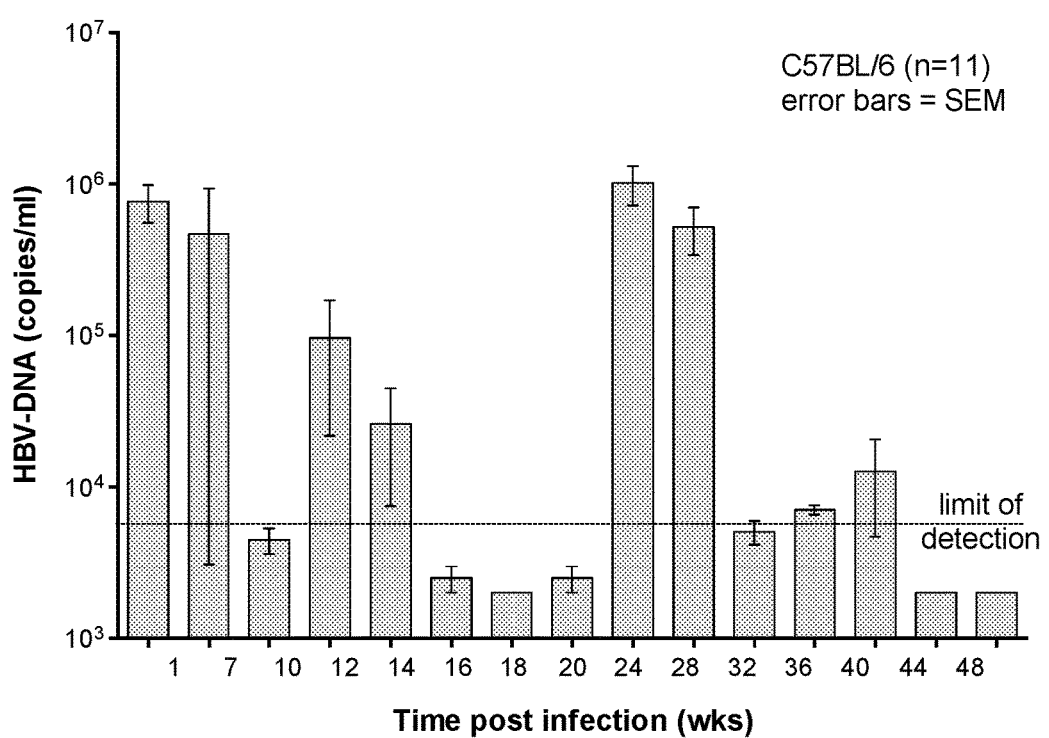
FIG. 2 shows the time course of serum HBV DNA levels in the serum of infected mice over a 40 week period. Despite apparent control of viremia, infected mice show a recrudescence in HBV viral replication with a transient spike in serum HBV DNA levels even at 24 weeks post-infection.

Using this technique, C57BL/6 mice (6-12 weeks old of either gender) were infected with HBV and they expressed surface antigen, core antigen, and e-antigen and demonstrated high levels of serum HBV DNA (see FIG. 1). Additionally, virions were identified in the serum of infected animals and histological examination of liver showed that approximately 20% of hepatocytes were infected with HBV (express HBcAg). This closely mimics human infection. Also, much like in human infection, mice started to control viraemia at 8 to 12 weeks post-infection, but HBV DNA could still be detected in the serum of mice beyond 24 weeks after infection (see FIG. 2). This indicates that the full replicative life cycle of HBV is being recapitulated in mouse hepatocytes and the episomal HBV transcriptional template is likely to persist in some hepatocytes giving rise to the recrudescence in viraemia observed at 24 weeks post-infection.

Example 2

Treatment of Mice with Birinapant

C57BL/6 mice were infected with HBV and 6 days after infection were treated with weekly doses of birinapnat (30 mg/kg administered intraperitoneally) or vehicle control (DMSO) for a total of 3 weeks (3 doses).

Figure 3:
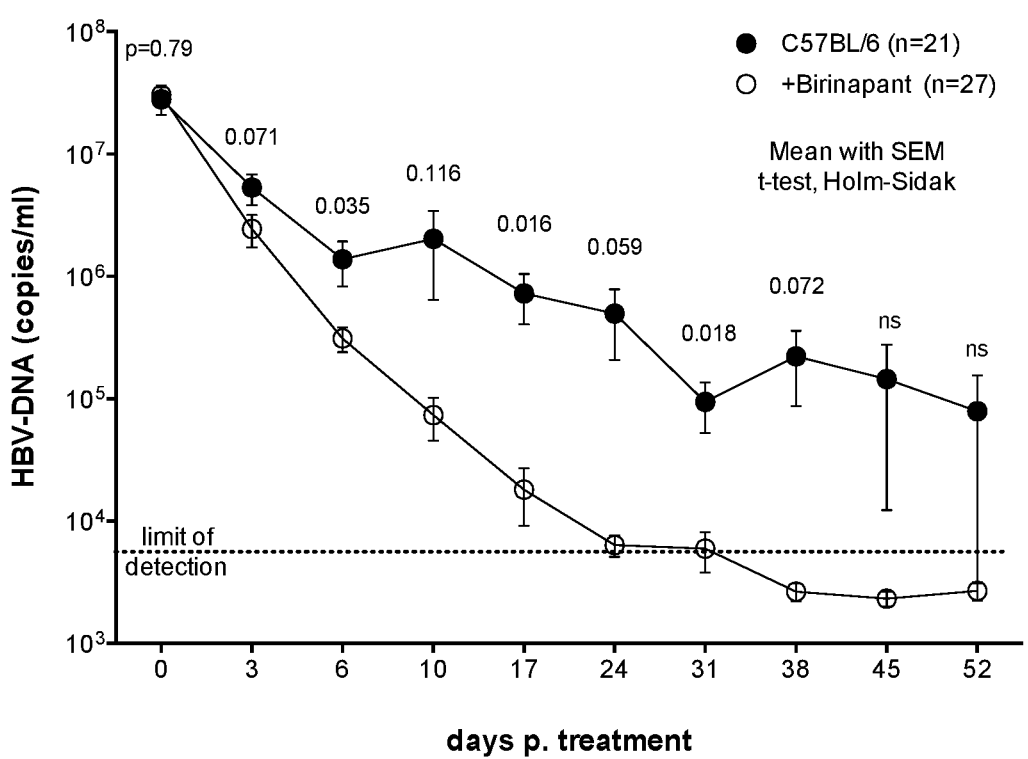
FIG. 3 shows HBV DNA serum levels in mice treated with Birinapant or vehicle control (DMSO).
Figure 4:
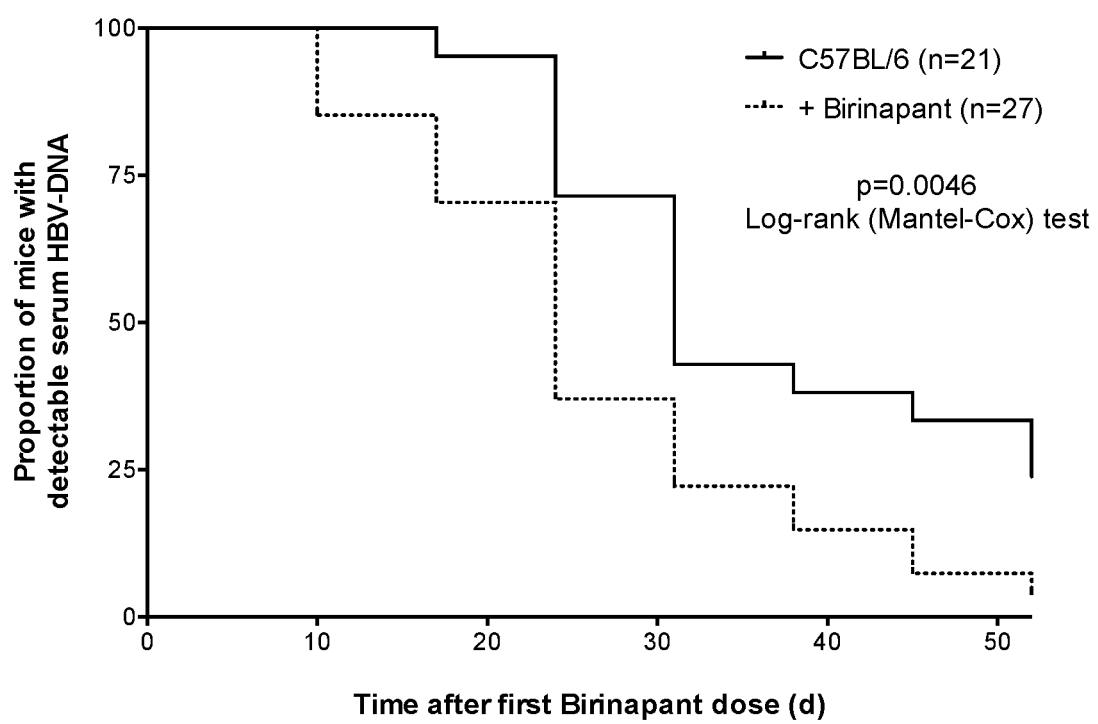
FIG. 4 shows a time to event (HBV clearance) graph comparing Birinapant and vehicle control treated (C57BL/6) HBV infected mice.

Six days post-HBV infection, mice were treated with birinapant or vehicle control. After a three doses of birinapant, HBV viral load was reduced by 2 logs compared to viral loads in mice treated with vehicle control. All birinapant-treated, HBV-infected mice had no detectable HBV DNA in their serum 39 days after the first dose of birinapant. On average, mice treated with vehicle control still had approximately $10^6$ copies of HBV DNA in their serum at this time point (see FIG. 3). It was found that 3 doses of birinapant had equivalent efficacy as 6 doses of birinapant in promoting HBV clearance. Birinapant treatment achieved HBV clearance as early as 10 days after the first treatment dose (see FIG. 4).

Example 3

Figure 5:
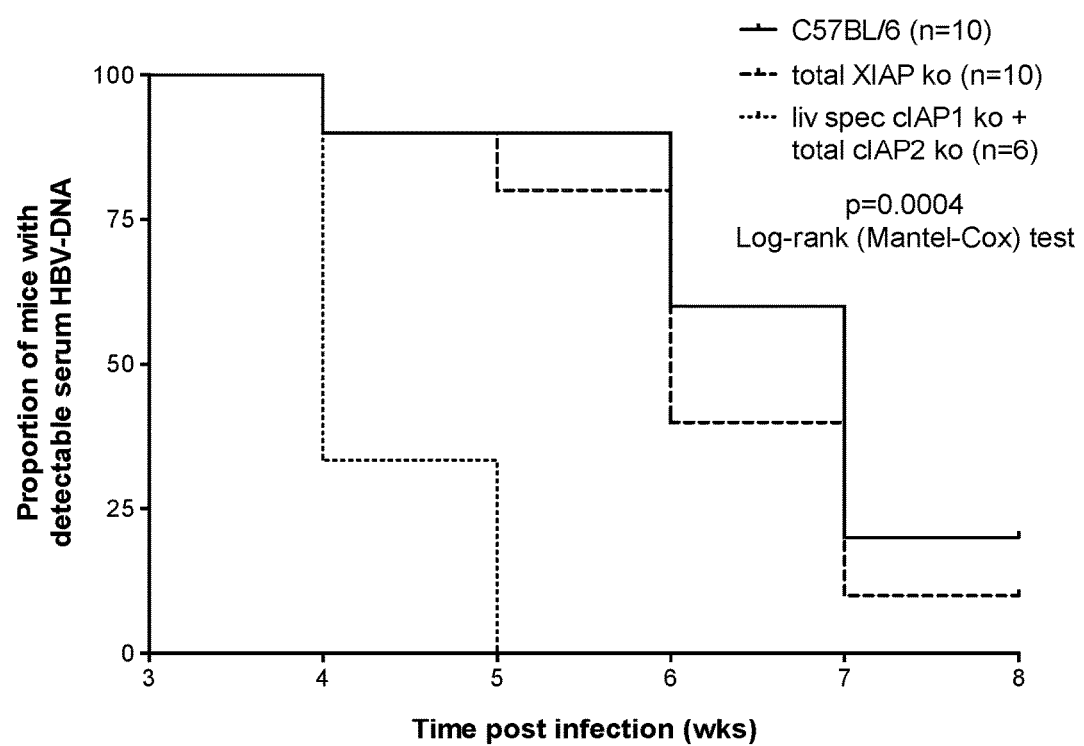
FIG. 5 shows that mice deficient in cIAP1 (liver specific deficiency), together with a total deficiency of cIAP2 in all organs, can clear HBV infection to a similar extent as wild-type mice treated with Birinapant. Dotted, solid red and solid blue lines indicate the number of wild-type mice, liver specific cIAP1 deficient plus total body cIAP2 deficient mice and XIAP deficient (total body) mice (%) clearing infection over time, respectively.

Genetic Targeting of cIAP1 and cIAP2 Recapitulated the HBV Clearance Kinetics Seen with Birinapant Treatment Gene targeted mice, which had a deficiency of cIAP1 (liver-specific deficiency) together with a deficiency of cIAP2 in all tissues, were able to clear HBV infection with similar kinetics to mice treated with birinapant (see FIG. 5).

Example 4

Activity of Birinapant Against HIV-1JR-CSF in Human Peripheral Blood Mononuclear Cells (PBMCs)

Methods
Virus Isolate

The HIV-1 isolate JR-CSF (Group M, Subtype B, CCR5-tropic, isolated from filtered cerebrospinal fluid of patient with AIDS dementia) was obtained from the NIAID AIDS Research and Reference Reagent Program. Low passage stocks of the virus were prepared using fresh human PBMCs and stored in liquid nitrogen. Pre-titered aliquots of the virus were removed from the freezer and thawed rapidly to room temperature in a biological safety cabinet immediately before use.

Anti HIV Efficacy Evaluation in Fresh Human PBMCs

Fresh human PBMCs, seronegative for HIV and HBV, were isolated from screened donors (Biological Specialty Corporation, Colmar, Pa.). Cells were pelleted/washed 2-3 times by low speed centrifugation and re-suspended in PBS to remove contaminating platelets. The Leukophoresed blood was then diluted 1:1 with Dulbecco's Phosphate Buffered Saline (DPBS) and layered over 14 mL of Lymphocyte Separation Medium (LSM; Cellgro® by Mediatech, Inc.; density 1.078+/−0.002 g/ml; Cat.#85-072-CL) in a 50 mL centrifuge tube and then centrifuged for 30 minutes at 600×g. Banded PBMCs were gently aspirated from the resulting interface and subsequently washed 2× with PBS by low speed centrifugation. After the final wash, cells were enumerated by trypan blue exclusion and re-suspended at $1 \times 10^6$ cells/mL in RPMI 1640 supplemented with 15% Fetal Bovine Serum (FBS), and 2 mM L-glutamine, 4 µg/mL Phytohemagglutinin (PHA, Sigma). The cells were allowed to incubate for 48-72 hours at 37° C. After incubation, PBMCs were centrifuged and re-suspended in RPMI 1640 with 15% FBS, 2 mM L-glutamine, 100 U/mL penicillin, 100 µg/mL streptomycin, and 20 U/mL recombinant human IL-2 (R&D Systems, Inc). IL-2 is included in the culture medium to maintain the cell division initiated by the PHA mitogenic stimulation. PBMCs were maintained in this medium at a concentration of $1-2 \times 10^6$ cells/mL with biweekly medium changes until used in the assay. Cells were kept in culture for a maximum of two weeks before being deemed too old for use in assays and discarded. Monocyte derived macrophages (MDMs) are depleted from the culture as the result of adherence to the tissue culture flask.

For the standard PBMC assay, PHA stimulated cells from at least two normal donors were pooled (mixed together), diluted in fresh medium to a final concentration of $1 \times 10^6$ cells/mL, and plated in the interior wells of a 96 well round bottom microplate at 50 µL/well ($5 \times 10^4$ cells/well). Pooling (mixing) of mononuclear cells from more than one donor was used to minimize the variability observed between individual donors, which results from quantitative and qualitative differences in HIV infection and overall response to the PHA and IL-2 of primary lymphocyte populations. Each plate contains virus/cell control wells (cells plus virus) and experimental wells (drug plus cells plus virus). In this in vitro assay, PBMC viability remains high throughout the duration of the incubation period. Therefore, infected wells are used in the assessment of both antiviral activity and cytotoxicity. Test drug dilutions were prepared at a 2× concentration in microtiter tubes and 100 µL of each concentration (nine total concentrations) are placed in appropriate wells using the standard format. 50 µL of a predetermined dilution of virus stock was placed in each test well (final MOI=0.1). The PBMC cultures were maintained for six days following infection at 37° C., 5% CO2. After this period, cell-free supernatant samples were collected for analysis of reverse transcriptase activity. Following removal of supernatant samples, compound cytotoxicity was measured by addition of MTS to the plates for determination of cell viability. Wells were also examined microscopically and any abnormalities were noted.

Reverse Transcription Activity Assay

A microtiter plate-based reverse transcriptase (RT) reaction was utilized (Buckheit et al., AIDS Research and Human Retroviruses 7:295-302, 1991). Tritiated thymidine triphosphate ($^3$H-TTP, 80 Ci/mmol, NEN) was received in 1:1 dH$_2$O:Ethanol at 1 mCi/ml. Poly rA:oligodTtemplate:primer (Pharmacia) was prepared as a stock solution by combining 150 µl poly rA (20 mg/ml) with 0.5 ml oligodT (20 units/ml) and 5.35 ml sterile dH$_2$O followed by aliquoting (1.0 ml) and storage at −20° C. The RT reaction buffer was prepared fresh on a daily basis and consisted of 125 µl 1.0 M EGTA, 125 µl dH$_2$O, 125 µl 20% Triton X100, 50 µl 1.0 M Tris (pH 7.4), 50 µl 1.0 M DTT, and 40 µl 1.0 M MgCl$_2$. The final reaction mixture was prepared by combining 1 part $^3$H-TTP, 4 parts dH$_2$O, 2.5 parts poly rA:oligodT stock and 2.5 parts reaction buffer. Ten microliters of this reaction mixture was placed in a round bottom microtiter plate and 15 µl of virus-containing supernatant was added and mixed. The plate was incubated at 37° C. for 60 minutes. Following incubation, the reaction volume was spotted onto DE81 filter-mats (Wallac), washed 5 times for 5 minutes each in a 5% sodium phosphate buffer or 2×SSC (Life Technologies), 2 times for 1 minute each in distilled water, 2 times for 1 minute each in 70% ethanol, and then dried. Incorporated radioactivity (counts per minute, CPM) was quantified using standard liquid scintillation techniques.

MTS Staining for PBMC Viability to Measure Cytoxicity

At assay termination, the assay plates were stained with the soluble tetrazolium-based dye MTS (CellTiter®96 Reagent, Promega) to determine cell viability and quantify compound toxicity. MTS is metabolized by the mitochondrial enzymes of metabolically active cells to yield a soluble formazan product, allowing the rapid quantitative analysis of cell viability and compound cytotoxicity. This reagent is a stable, single solution that does not require preparation before use. At termination of the assay, 10-25 µL of MTS reagent was added per well (10% final concentration based on volume) and the microtiter plates were then incubated for 4-6 hrs at 37° C., 5% CO$_2$ to assess cell viability. Adhesive plate sealers were used in place of the lids, the sealed plate was inverted several times to mix the soluble formazan product and the plate was read spectrophotometrically at 490/650 nm with a Molecular Devices Vmax or SpectraMax Plus plate reader.

Data Analysis

Using an in-house computer program, the PBMC data analysis includes the calculation of IC$_{50}$ (50% inhibition of virus replication), IC$_{90}$ (90% inhibition of virus replication), IC$_{95}$ (95% inhibition of virus replication), TC$_{50}$ (50% cytotoxicity), TC$_{90}$ (90% cytotoxicity), TC$_{95}$ (95% cytotoxicity) and therapeutic index values (TI=TC/IC; also referred to as Antiviral Index or AI). Raw data for both antiviral activity and toxicity with a graphical representation of the data are provided below.

Results

Figure 6:
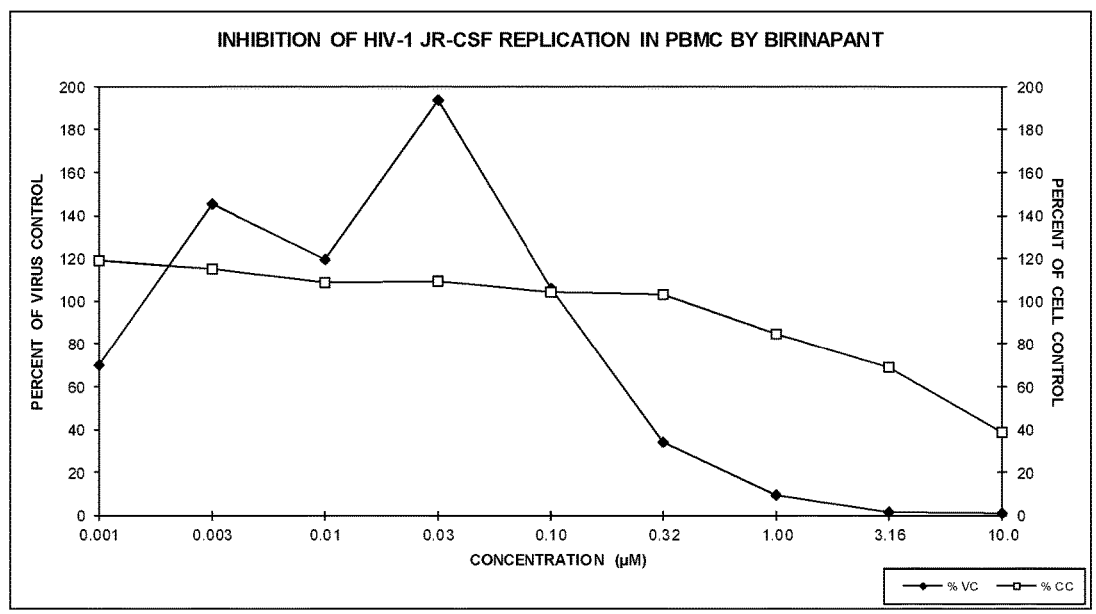
FIG. 6 Inhibition of HIV-1 JR-CSF replication in PBMC by Birinapant
Figure 7:
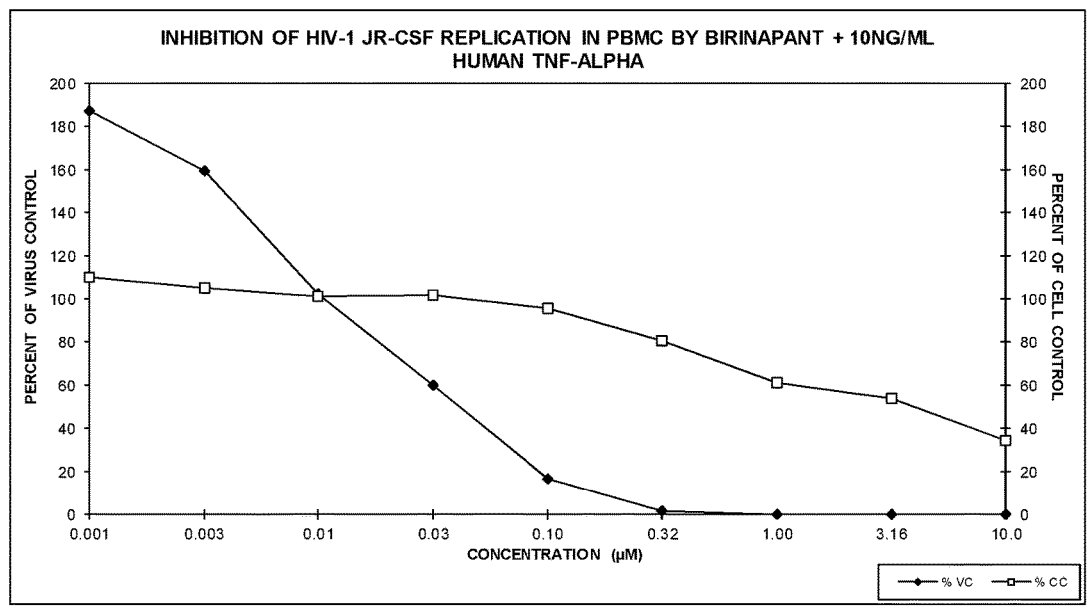
FIG. 7 Inhibition of HIV-1 JR-CSF replication in PBMC by Birinapant+ 10 ng/ml TNF-α

Birinapant, with and without a fixed concentration of TNF-α, was evaluated for antiviral efficacy against HIV-1 and the results are summarised in Table 1. In addition, the inhibition of HIV JR_CSF replication in PBMC by various concentrations of birinapant alone and in combination with 10 ng/ml TNF-α are shown in FIGS. 6 and 7 respectively.

TABLE 1

Activity of Birinapant ± TNF-α Against HIV-1JR-CSF in PBMCs

| Compound | High-Test Concentration | $IC_{50}$ | $TC_{50}$ | Antiviral Index ($TC_{50}/IC_{50}$) |
|---|---|---|---|---|
| Birinapant | 10 μM | 0.25 | 6.47 | 26.1 |
| Birinapant ± TNF-α | 10 μM + fixed 10 ng/mL | 0.04 | 3.98 | 101 |
| AZT | 1,000 nM | 1.71 | >1,000 | >584 |

Birinapant demonstrated antiviral activity against HIV-1 as well as some cytotoxicity in PBMC. In the presence of a fixed concentration (10 ng/mL) of TNF-α, there was a 6-fold increase in antiviral potency. The 1.6-fold increase in cytotoxicity is within the expected biological variability of the assay. TNF-α alone exerted a 35% reduction in HIV replication in this assay and did not affect cell viability using the MTS endpoint.

Example 5

Activity of Birinapant Against HIV Infected Cells

Methods.

Isolation and Activation. PBMCs from healthy donors were isolated via Ficoll (GE) gradient centrifugation and depleted of CD8+ cells using magnetic beads (Miltenyi). Remaining PBMCs were either maintained in a naïve state, or activatedin PHA (10 μg/mL) and cultured in RF10 (RPMI, 10% FCS, 2% glutamine), supplemented with IL-2 (10 U/mL) and IL-7 (25 ng/mL) for 3 days.

HIV Infection. Activated PBMCs were infected with HIV NL4.3 (GFP+, nefdeficient) at an MOI of 0.1 at 37° C. for 2 hours, or left uninfected. Following incubation, cells were washed 3 times in PBS and resuspended in RF10, supplemented with IL-2 and IL-7, and cultured at $1 \times 10^6$ cells/mL for a further 3 days.

Birinapant Treatment. PBMCs were supplemented with fresh media, followed by treatment with Birinapant (0.1 μM, 1 μM, or 10 μM), or DMSO alone (1% final concentration), for 6 hours or 24 hours. Following treatment, cells were fixed in a final concentration of 2% (w/v) paraformaldehyde.

FACS. Fixed cells were permeabilised using PermWash (BD) and stained at 4° C. for 1 hour with antibodies directed against CD4 (APC-H7; 1:20), CD3 (PE-Cy7, 1:40) and Active Caspase 3 (AF647, 1:25) (all antibodies purchased from BD).

Results

Figure 8:
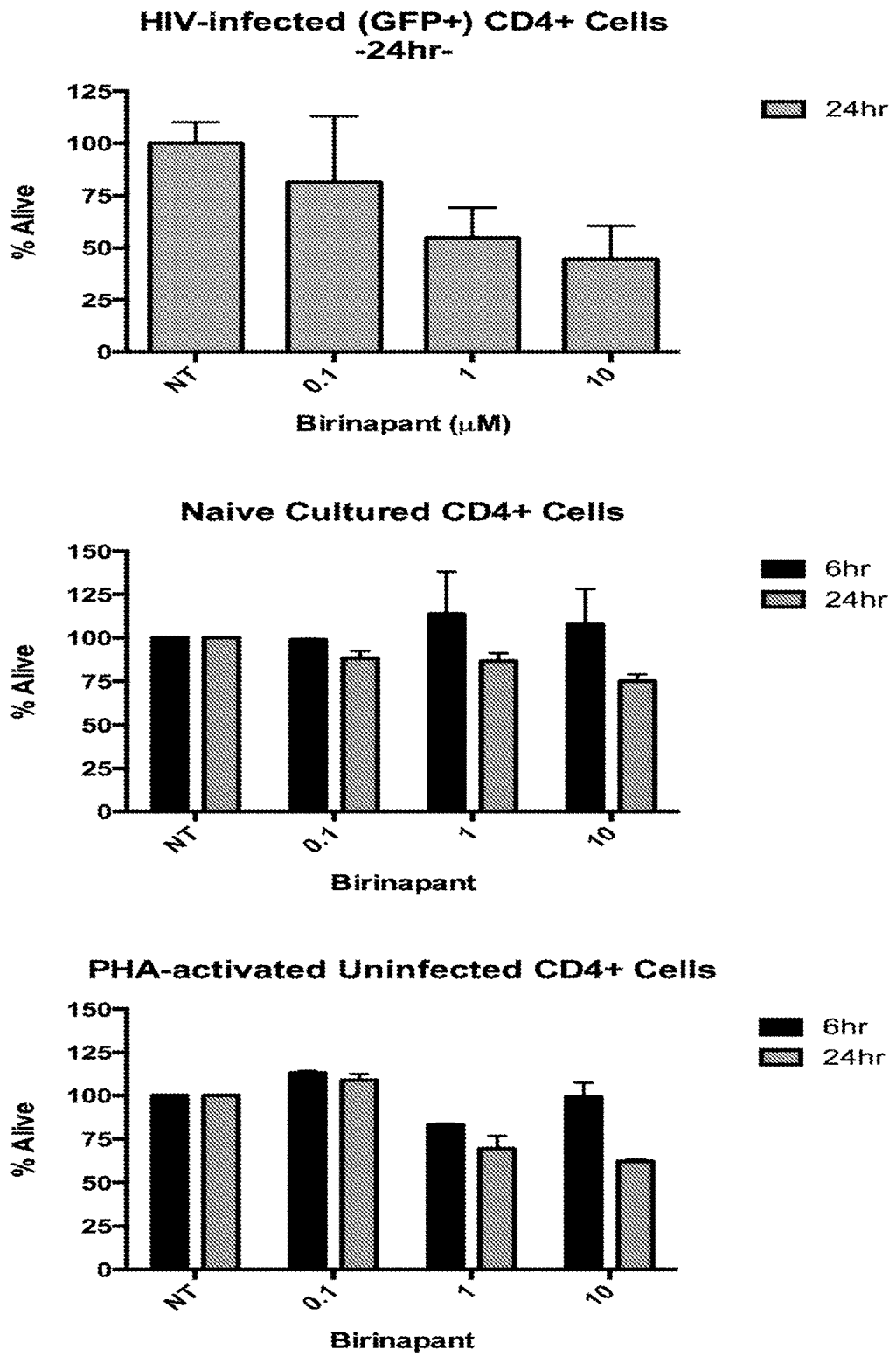
FIG. 8. PHA-activated PBMCs, isolated from two healthy donors, were left uninfected or infected with HIV NL4.3 (GFP+) and then treated with Birinapant or vehicle control (NT) for 6 hr or 24 hr at indicated concentrations. Additionally unifected naïve PBMCs were treated with Birinapant or vehicle control. FACS analysis of the proportion of living (Active-Caspase 3 negative) a) HIV-infected (GFP+) culturedCD4+ lymphocytes following 24 hr Birinapant treatment, relative to living infected cells prior to treatment; Proportion of living b) naïve cultured or c) PHA-activated, uninfected CD4+ lymphocytes following 6 hr or 24 hr Birinapant treatment, relative to untreated cells.

The results are shown in FIG. 8. After a single dose of 10 uM birinapant, 55% of HIV infected cells die within 24 hours. Birinapant has minimal effect on the viability of naïve cells and a small effect on activated T cells.

Example 5

Activity of Birinapant Against *Mycobacterium tuberculosis* Infection

Figure 9:
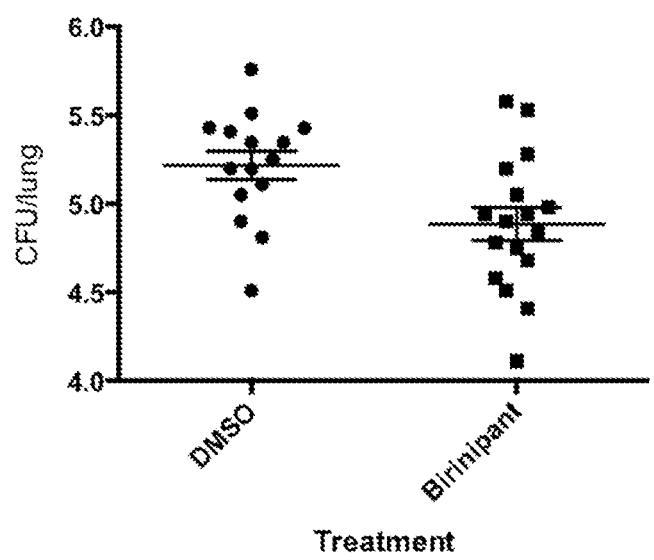
FIG. 9 *Mycobacterium tuberculosis* bacterial burden (CFU/lung $Log_{10}$), in *M. tuberculosis* infected mice treated with Birinipant (n=17, given as an intraperitoneal injection, at 30 µg/g at weekly intervals×3) in comparison to DMSO control (n=15), showing a significant reduction of 0.33 $Log_{10}$ CFU/lung (P=0.012).

A total of 32 mice were infected with *Mycobacterium tuberculosis* (strain H37Rv) and after 4 weeks of rest, 17 mice were treated with Birinapant (via intraperitoneal injection, at 304 g) and 15 mice were treated with DMSO, both given at weekly dosing. After three doses, mice were euthanized and lungs were taken, homogenised and the homogenate plated at serial dilutions on Middlebrook 7H11 agar plates. The colony forming units (CFU) was determined after 3 weeks of culturing and the results are shown in FIG. 9.

Upon dissection of the mice, macroscopically, it was noted that the lungs of the Birinapant treated group appeared pink, uniform and healthier in appearance. The spleens were also enlarged in comparison with the DMSO group. Results showed a statistically significant reduction (p=0.012) in the bacterial burden in the Birinapant group (0.33 $Log_{10}$ CFU/lung).

Example 6

Effect of Antagonizing TNF-α Cytokine on Activity of Birinapant

Mice were infected with HBV and then injected (intraperitoneally) with TNF-α antagonizing antibodies at various indicated time points. As a control, another cohort of HBV infected mice were injected with an irrelevant IgG1 isotype control antibody.

Figure 10:
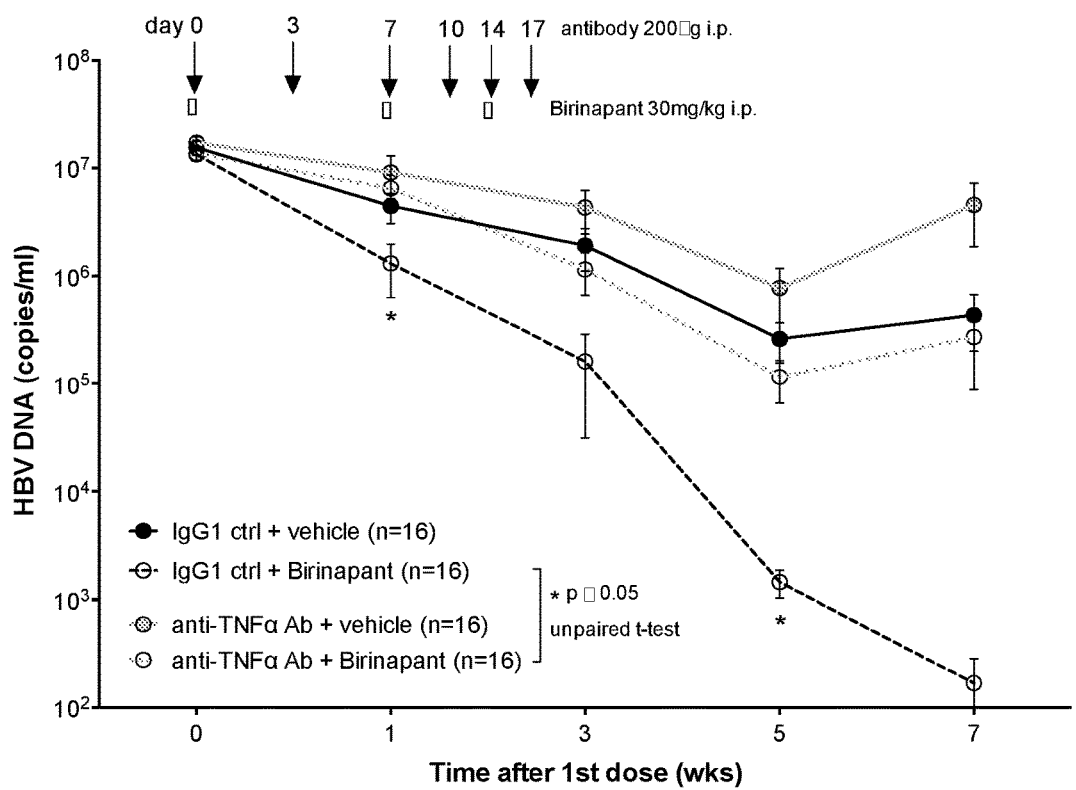
FIG. 10 Antagonizing TNF-α cytokine abrogates the effectiveness of birinipant

The results of this experiment are shown in FIG. 10. As is shown in this Figure antagonizing the activity of TNF-α abrogates the efficacy of birinapant. Therefore brinapant is, at least in part, promoting the ability of endogenously produced TNF-α to kill infected hepatocytes and or reduce HBV levels.

Birinapant appears to facilitate and enhance the activity of endogenously produced TNF-α and promote the ability of this cytokine to eliminate infection. IAPB are also known to modulate endogenous TRAIL signalling (another TNF superfamily member) and therefore birinapant, through its ability to antagonize IAPB, may also promote the capacity of TRAIL to eradicate infected cells.

The data indicates that birinapant promotes the activity of endogenous TNF-α and facilitates the ability of this cytokine to eradicate infected cells. The combination of birinapant and an exogneous TNF-α like molecule administered simultaneously would then likely show a pronounced increase in efficacy in the eradication of HBV compared to birinapant alone. (This was demonstrated with HIV in Example 4). Due to its toxicity TNF-α is difficult to administer to humans but the related molecule TRAIL has been used in human trials and was not found to be toxic. Therefore the combination of IAP antagonists of the present invention, and in particular birinapant, and TRAIL could be used to enhance the efficacy of birinapant and promote clearance of infected cells.

Example 7

Activity of Other IAP Antagonists

Mice were infected with HBV and treated with either birinapant or another IAP antagonist (SMAC mimetic) called GT13072 described Fan et at 2013 (20).

C57BL/6 mice were infected with HBV and 6 days after infection mice were divided randomly into 3 cohorts. One cohort was treated with birinapant (as described in Example 2), another cohort was treated with weekly doses of GT13072 (15 mg/kg administered intraperitoneally—a total of 3 doses over 3 weeks) and a 3rd cohort was treated with a vehicle control. The results are shown in FIG. 11.

Figure 11:
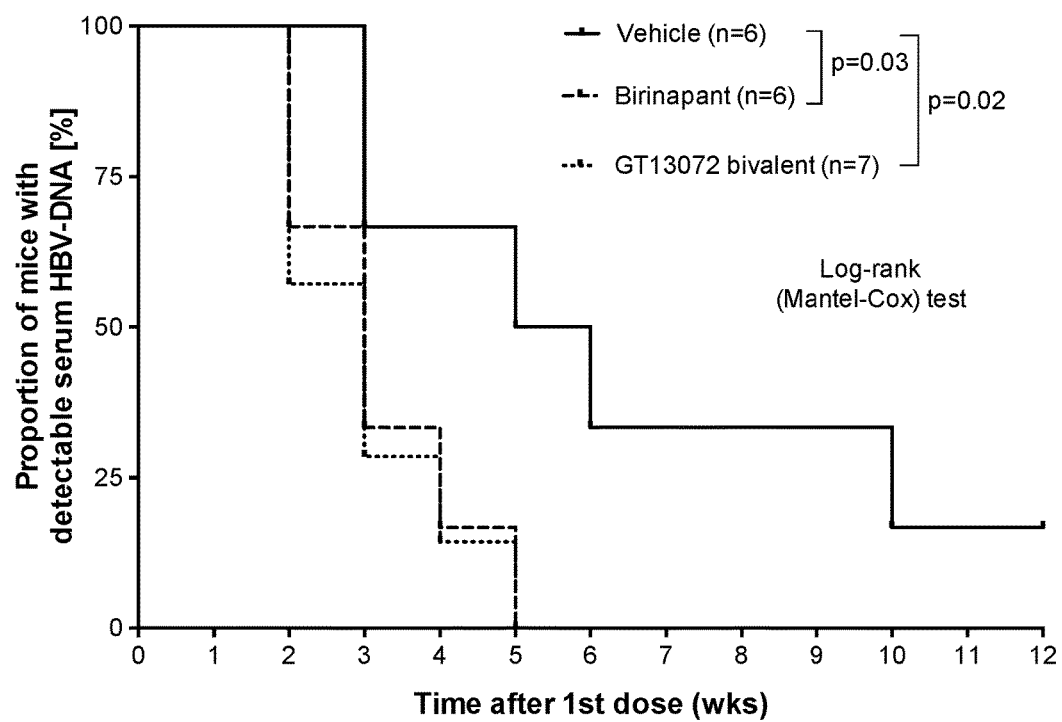
FIG. 11 Results of experiments with SMAC mimetics other than birinipant

The result shown in FIG. 11 show that the ability of birinapant to clear HBV infection is shared by other SMAC mimetics. Therefore SMAC mimetics/IAP antagonists as a class of drugs are efficacious in the treatment of intracellular infections.

Example 8

Activity of Birinapant Against *Legionella pneumophila* Infection

Figure 12:
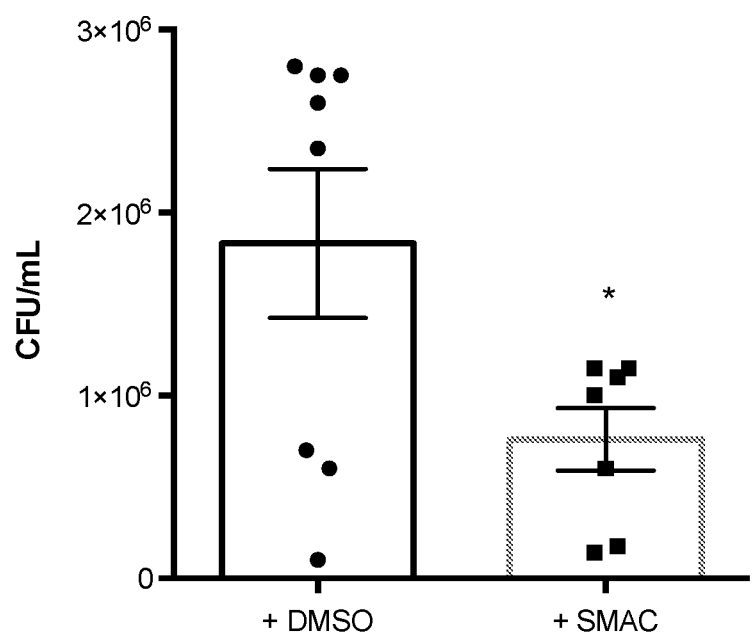
FIG. 12 *Legionella pneumophila* bacterial burden in lungs of infected mice (CFU/ml) administered birinapant (squares) or vehicle control (circles). Each point represents an animal, error bars represent SEM. *P<0.05.

Six to 12 week old C57BL/6 mice were infected with *Legionella pnemophila* ($2.5 \times 10^6$ colony forming units in 50 µl of phosphate buffered saline) intranasally. Six hours after infection mice were treated with a single dose of birinapant (10 mg/Kg administered intraperitioneally—squares) or treated with vehicle control (circles). Two days after infection lungs were harvested from animals and the number of bacteria was quantified by culture. The results are shown in FIG. 12 where each point represents an animal, error bars represent SEM. *$P<0.05$. The data show that birinapant treatment promotes the clearance of *Legionella pnemophila* and disease resolution compared to control treatment.

Example 9

Effect of Entecavir Combined with Birinapant

C57Bl/6 mice were infected with HBV and 6 days later treatment was commenced with birinapant alone (30 mg/Kg given once weekly intraperitoneally for 2 weeks totalling 2 doses) or entecavir (3.2 mg/Kg administered once a day by gavage for 8 days totalling 8 doses) or birinapant plus entecavir at the doses and for the durations indicated above.

Figure 13:
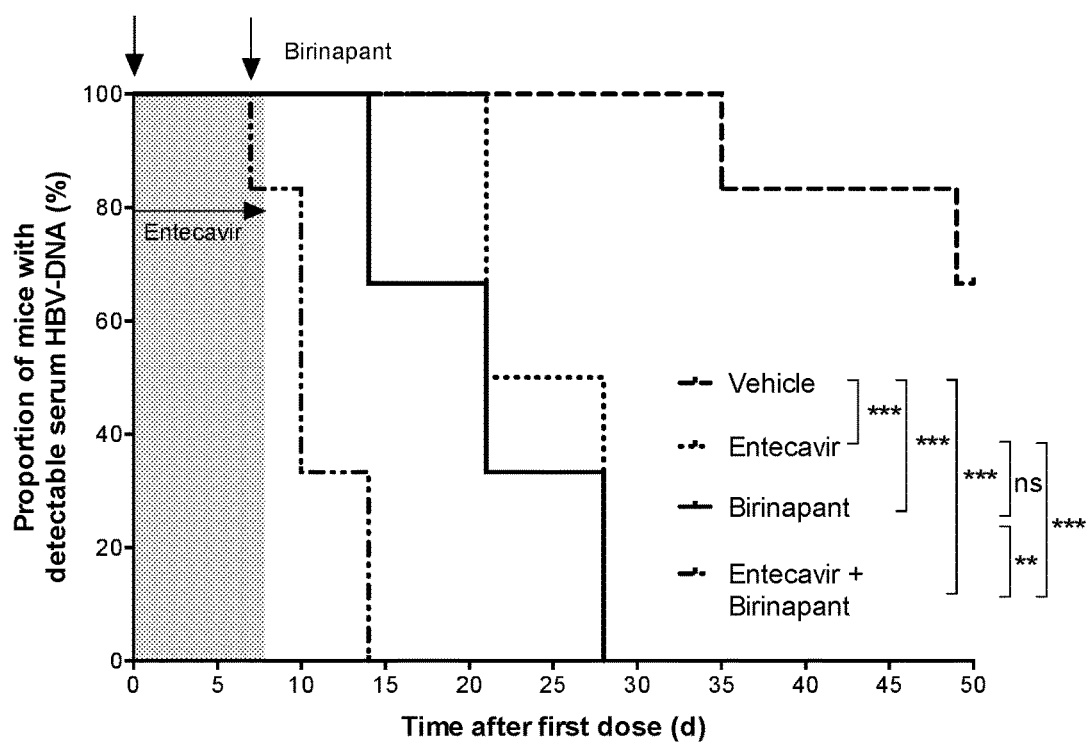
FIG. 13 shows the results of the treatment of HBV infected mice with Entacavir, birinapant and entacavir combined. *p<0.001, p<0.01, ns=not significant.

The results are shown in FIG. 13 where the grey shaded area indicates duration of entecavir treatment and arrows indicate birinapant doses. *$p<0.001$, $p<0.01$, ns=not significant, six mice in each group and the findings were reproduced in 3 independent experiments.

As is clear from these results combining birinapant with the nucleoside analogue entecavir improves efficacy in promoting the clearance of serum HBV DNA in infected mice compared to the efficacy of either drug administered as a sole agent.

Example 10

Effect of TRAIL Combined with Birinapant

Figure 14:
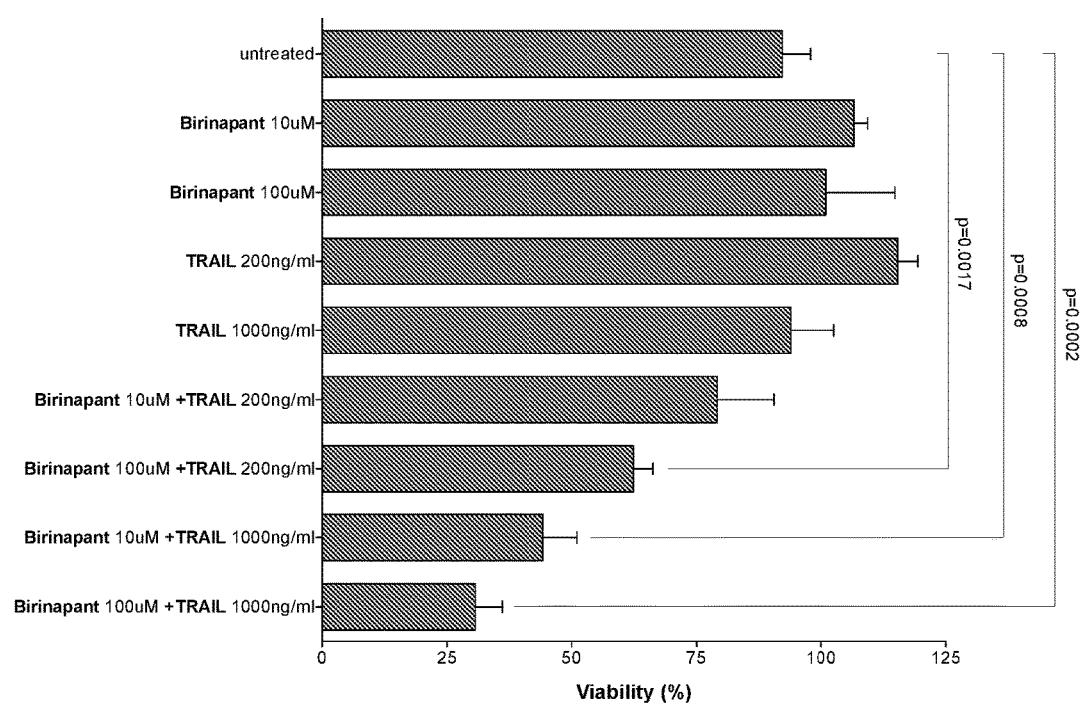
FIG. 14 shows the results of the treatment of primary human hepatocytes infected in vitro with HBV using an adenoviral delivery system with TRAIL, birinapant and a combination of TRAIL and birinapant.

Primary human hepatocytes were infected in vitro with HBV using an adenoviral delivery system as previously described (Chin R, Earnest-Silveira L, Koeberlein B, Franz S, Zentgraf H, Bowden S, Bock C-T, Torresi J. Modulation of MAPK pathways and cell cycle byreplicating hepatitis B virus: factors contributing tohepatocarcinogenesis. J Hepatology 2007; 47:325-37). The delivery system included a green fluorescent protein marker so that the proportion of infected cells could be quantified. Using this system approximately 100% of hepatocytes were infected with HBV. Cells were rested for 2 days after infection and then they were treated with the indicated agents. Forty eight hours after treatment cell viability was assessed using Cell-Titer-Glo® (Promega, Madison Wis. USA) according to the manufacturer's protocol. This experiment was performed in triplicate and repeated 2 times using 2 independent donors. The highest CellTiter-Glo result from one of the triplicate untreated samples was used to set the 100% viability mark. The result are shown in FIG. 14

From the results of this experiment it was clear that TRAIL, when used as a single agent, has virtually no efficacy in promoting the death of human primary hepatocytes infected with HBV. The present inventors have shown that birinapant is ineffective at controlling HBV infection in vivo when TNF-α signalling is abrogated. Equally, in the absence of TNF-α, birinapant is not effective in killing infected hepatocytes in vitro. However, the combination of TRAIL and birinapant very effectively kill primary human hepatocytes infected with HBV even in the absence of TNF-α. These data indicate that TRAIL is able to promote the efficacy of birinapant in eliminating infected cells and that birinapant's in vivo efficacy may be promoted with concurrent administration of a TRAIL agonist.

SUMMARY

The results show that birinapant treatment clears HBV infection. Equally, gene targeted deletion of IAPB promotes clearance of HBV infection. Collectively, the data show that any method of antagonizing IAPB has therapeutic efficacy in eliminating HBV infection. No toxicity related to birinapant treatment in HBV-infected mice was identified and IAP-deficient animals infected with HBV also appeared healthy. These data indicate that antagonizing IAPB sensitizes infected cells to death, but it does not sensitize normal or uninfected cells to programmed cell death. Furthermore, inhibition of IAPB prevented deleterious inflammatory responses. These results also show activity of birinapant against HIV, *M. tuberculosis* and *Legionella pneumophila* infected cells. It is believed that these results can be readily extended to other infections that persist in host cells, including HCV, HPV, CMV, and other intracellular viruses, bacteria, fungi, yeast and parasites.

REFERENCES

1. Du C, Fang M, Li Y, Li L, Wang X. Smac, a mitochondrial protein that promotes cytochrome c-dependent caspase activation by eliminating IAP inhibition. Cell. 2000; 102: 33-42.
2. Vince J E, Wong W W, Khan N, Feltham R, Chau D, Ahmed A U, et al. IAP antagonists target cIAP1 to induce TNF alpha-dependent apoptosis. Cell. 2007; 131: 682-93.
3. Vince J E, W. W. Gentle, I. Lawlor, K. E. Allam, R. O'Reilly, L. Mason, K. Gross, O. Ma, S. Guarda, G. Anderton, H. Castillo, R. Hacker, G. Silke, J. Tschopp, J. Inhibitor of Apoptosis Proteins Limit RIP3 Kinase-Dependent Interleukin-1 Activation. Immunity. 2012; 36: 215-27.
4. Lamkanfi M, Dixit V M. Manipulation of host cell death pathways during microbial infections. Cell Host Microbe. 2010; 8: 44-54.
5. Yatim N, Albert M L. Dying to replicate: the orchestration of the viral life cycle, cell death pathways, and immunity. Immunity. 2011; 35: 478-90.
6. Mocarski E S, Upton J W, Kaiser W J. Viral infection and the evolution of caspase 8-regulated apoptotic and necrotic death pathways. Nature reviews. 2012; 12: 79-88.
7. Lin Y J, Huang L R, Yang H C, Tzeng H T, Hsu P N, Wu H L, et al. Hepatitis B virus core antigen determines viral persistence in a C57BL/6 mouse model. Proceedings of the National Academy of Sciences of the United States of America. 2010; 107: 9340-5.
8. Huang L R, Wu H L, Chen P J, Chen D S. An immunocompetent mouse model for the tolerance of human chronic hepatitis B virus infection. Proceedings of the National Academy of Sciences of the United States of America. 2006; 103: 17862-7.
9. Ebert G, Poeck H, Lucifora J, Baschuk N, Esser K, Esposito I, et al. 5' Triphosphorylated small interfering RNAs control replication of hepatitis B virus and induce an interferon response in human liver cells and mice. Gastroenterology. 2011; 141: 696-706, el-3.
10. Cooper A M, Torrado E. Protection versus pathology in tuberculosis: recent insights. Current opinion in immunology. 2012; 24: 431-7.
11. Saunders B M, Britton W J. Life and death in the granuloma: immunopathology of tuberculosis. Immunol Cell Biol. 2007; 85: 103-11.
12. Lin P L, Flynn J L. Understanding latent tuberculosis: a moving target. J Immunol. 2010; 185: 15-22.
13. Abebe M, Kim L, Rook G, Aseffa A, Wassie L, Zewdie M, et al. Modulation of cell death by *M. tuberculosis* as a strategy for pathogen survival. Clin Dev Immunol. 2011; 2011: 678570.
14. Behar S M, Divangahi M, Remold H G. Evasion of innate immunity by *Mycobacterium tuberculosis*: is death an exit strategy? Nat Rev Microbiol. 2010; 8: 668-74.
15. Melki M T, Saidi H, Dufour A, Olivo-Marin J C, Gougeon M L. Escape of HIV-1-infected dendritic cells from TRAIL-mediated NK cell cytotoxicity during NK-DC cross-talk—a pivotal role of HMGB1. PLoS Pathog. 2010; 6: e1000862.
16. Gougeon M L, Piacentini M. New insights on the role of apoptosis and autophagy in HIV pathogenesis. Apoptosis. 2009; 14: 501-8.
17. Herbein G, Khan K A. Is HIV infection a TNF receptor signalling-driven disease? Trends Immunol. 2008; 29: 61-7.
18. Kaminskyy V, Zhivotovsky B. To kill or be killed: how viruses interact with the cell death machinery. Journal of internal medicine. 2010; 267: 473-82.
19. Shedlock D J, Hwang D, Choo A Y, Chung C W, Muthumani K, Weiner DB. HIV-1 viral genes and mitochondrial apoptosis. Apoptosis. 2008; 13: 1088-99.
20. Fan L X, Zhou X, Sweeney W E Jr, Wallace D F, Avner E D, Grantham J J, Li X. Smac-mimetic-induced epithelial cell death reduces the growth of renal cysts. J Am Soc Nephrol 2013; 24:2010-22.

SAMPLE EMBODIMENTS

Sample embodiments of the disclosure include:
1. A method of treating an intracellular infection in a subject, the method comprising administering to the subject an IAP antagonist.
2. The method as defined in embodiment 1 wherein the IAP is cIAP1 and/or cIAP2.
3. The method as defined in embodiment 1 or 2 wherein the antagonist is a Smac mimetic.
4. The method as defined in embodiment 3, wherein the Smac mimetic comprises one or more of the following characteristics:
   (a) the Smac mimetic is bivalent;
   (b) the Smac mimetic derepresses XIAP-mediated caspase-3 repression;
   (c) the Smac mimetic degrades cIAP-1 not bound to TRAF2 as well as cIAP1 bound to TRAF2;
   (d) the Smac mimetic degrades cIAP-2 bound to TRAF2 but does not degrade cIAP-2 not bound to TRAF2;
   (e) the Smac mimetic weakly degrades cIAP-2 not bound to TRAF2 relative to degradation of cIAP-2 bound to TRAF; and
   (f) the Smac mimetic has the general structure [P1-P2-P3-P4] or [P1-P2-P3-P4]-L-[P1'-P2'-P3'-P41, wherein P1-P2-P3- and P1'-P2'-P3'- correspond to peptide replacements or peptidomimetics of the N-terminal Ala-Val-Pro- tripeptide of mature Smac and P4 and P4' correspond to amino acid replacements of Phe, Tyr, Ile, or Val, and L is a linking group, or bond, covalently linking [P1-P2-P3-P4] to [P1'-P2'-P3'-P4'].
5. The method as defined in embodiment 3 or 4 wherein the Smac mimetic is birinapant.
6. The method as defined in embodiment 1 wherein the antagonist reduces expression of the IAP gene.
7. The method as defined in embodiment 6 wherein the IAP gene is the cIAP1 or cIAP2 gene.
8. The method defined in embodiment 6 or 7 wherein the antagonist is siRNA, shRNA or miRNA.
9. The method as defined in embodiment 8 wherein the siRNA, shRNA or miRNA is targeted against a sequence selected from the group consisting of NCBI Reference Sequence: NM_001166.4, NCBI Reference Sequence: NM_001256163.1, NCBI Reference Sequence: NM_001256166.1, GenBank: DQ068066.1, NCBI Reference Sequence: NM_001165.4, NCBI Reference Sequence: NM_182962.2, GenBank: BC037420.1, NCBI Reference Sequence: NM_001167.3, NCBI Reference Sequence: NM_001204401.1, NCBI Reference Sequence: NR_037916.1, and NCBI Reference Sequence: NG_007264.1
10. The method as defined in any one of embodiments 1 to 9 wherein the infection is caused by a virus selected from the group consisting of Human papillomaviruses, Herpes viruses including herpes simplex 1/2, varicella zoster, EBV, CMV, HHV-6/7, HTLV, Human papovaviruses including JC virus and BK virus, adeno and parvoviruses, HIV, HBV and HCV.
11. The method as defined in any one of embodiments 1 to 9 wherein the infection is caused by a bacteria selected from the group consisting of *Salmonella* spp., *Ehrlichia* spp., *Mycobacteria* spp., *Spirochetes, Legionella* spp., *Listeria* spp., *Rickettsia* spp., *Chlamydia* spp., *Mycoplasma* spp., *Coxiella* spp., *Yersinia* spp., *Francisella* spp., *Brucella* spp., *Neisseria* spp, and *Nocardia* spp.
12. The method as defined in any one of embodiments 1 to 9 wherein the infection is caused by a fungi or yeast selected from the group consisting of *Histoplasma* spp., *Aspergillus* spp., *Cryptococcus* spp., and *Pneunocystis jirovecii*,
13. The method as defined in any one of embodiments 1 to 9 wherein the infection is caused by a protozoa selected from the group consisting of Trypanosomatids including *Leishmania* spp., Apicomplexans including liver forms of *Plasmodium* spp., *Toxoplasma* spp., and *Cryptosporidium* spp.
14. The method as defined in embodiment 10 wherein the virus is HIV and the IAP antagonist is administered in combination with TNF-α.
15. The method of any of the preceding embodiments wherein the IAP antagonist is co-administered with a TNF-α or other TNF receptor agonist.
16. The method of any of the preceding embodiments wherein the IAP antagonist is co-administered with TRAIL.

17. The method of any of embodiments 1 to 10 wherein the TAP antagonist is co-administered with an anti-viral nucleoside analogue.
16. The method of embodiment 17 wherein the nucleoside analogue is Entacavir.
19. The use of an TAP antagonist in the treatment of an intracellular infection in a subject.
20. The use of an TAP antagonist in the preparation of a medicament for the treatment of an intracellular infection in a subject.

The invention claimed is:

1. A method of treating a persistent intracellular infection in which tumor necrosis factor (TNF) is produced, the method comprising administering to a subject in need thereof an effective amount of an Inhibitor of Apoptosis (IAP) antagonist
   wherein the intracellular infection is a viral infection caused by a virus selected from the group consisting of Human papillomaviruses, Herpes viruses, Human papovaviruses, adenoviruses, parvoviruses, human immunodeficiency virus (HIV), hepatitis B virus (HBV), hepatitis C virus (HCV) and human T-cell lymphotropic virus (HTLV), or
   wherein the intracellular infection is a bacterial infection caused by a bacteria selected from the group consisting of *Salmonella* spp., *Ehrlichia* spp., *Mycobacteria* spp., *Spirochetes, Legionella* spp *Listeria* spp., *Rickettsia* spp., *Chlamydia* spp., *Mycoplasma* spp., *Coxiella* spp., *Yersinia* spp., *Francisella* spp., *Brucella* spp., *Neisseria* spp, and *Nocardia* spp.; and
   wherein the IAP antagonist is a monovalent IAP antagonist, a bivalent IAP antagonist, a nonpeptidomimetic IAP antagonist, or an IAP antagonist that reduces expression of an IAP gene.
2. The method as claimed in claim 1 wherein the IAP antagonist is an antagonist for cIAP1 and/or cIAP2.
3. The method as claimed in claim 1 wherein the IAP antagonist is a second mitochondria-derived activator of caspase (Smac) mimetic.
4. The method as claimed in claim 3, wherein the Smac mimetic exhibits one or more of the following characteristics:
   a. the Smac mimetic is bivalent;
   b. the Smac mimetic derepresses X-linked inhibitor of apoptosis-mediated (XIAP-mediated) caspase-3 repression;
   c. the Smac mimetic degrades cIAP-1 not bound to TNF receptor associated factor 2 (TRAF2) and cIAP1 bound to TRAF2;
   d. the Smac mimetic degrades cIAP-2 bound to TRAF2 but does not degrade cIAP-2 not bound to TRAF2;
   e. the Smac mimetic weakly degrades cIAP-2 not bound to TRAF2 relative to degradation of cIAP-2 bound to TRAF; and
   f. the Smac mimetic has the general structure [P1-P2-P3-P4] or [P1-P2-P3-P4]-L-[P1'-P2'-P3'-P4'], wherein P1-P2-P3- and P1'-P2'-P3'- correspond to peptide replacements or peptidomimetics of the N-terminal Ala-Val-Pro- tripeptide of mature Smac and P4 and P4' correspond to amino acid replacements of Phe, Tyr, Ile, or Val, and L is a linking group, or bond, covalently linking [P1-P2-P3-P4] to [P1'-P2'-P3'-P4'].
5. The method as claimed in claim 4 wherein the Smac mimetic is birinapant.
6. The method as claimed in claim 1 wherein the IAP antagonist reduces expression of the IAP gene.
7. The method as claimed in claim 6 wherein the IAP gene is the cIAP1 or cIAP2 gene.
8. The method as claimed in claim 6 wherein the IAP antagonist is small interfering RNA (siRNA), small hairpin RNA (shRNA) or microRNA (miRNA).
9. The method as claimed in claim 8 wherein the siRNA, shRNA or miRNA is targeted against a gene encoding cIAP1, cIAP2, or XIAP.
10. The method as claimed in claim 1 wherein the infection is caused by a virus selected from the group consisting of human immunodeficiency virus (HIV), hepatitis B virus (HBV) and human T-cell lymphotropic virus (HTLV).
11. The method as claimed in claim 1 wherein the infection is caused by a bacteria selected from the group consisting of *Mycobacteria* spp., and *Legionella* spp.
12. The method as claimed in claim 10 wherein the intracellular infection is a viral infection caused by HIV and the method further comprises administering TNF-α.
13. The method of claim 1 further comprising administering a TNF receptor agonist.
14. The method of claim 1 further comprising administering NF-related apoptosis-inducing ligand (TRAIL).
15. The method of claim 1 further comprising administering an anti-viral nucleoside analogue.
16. The method of claim 15 wherein the nucleoside analogue is Entacavir.
17. The method of claim 1 further comprising administering TNF-α.
18. The method of claim 1, wherein the IAP antagonist is a monovalent IAP antagonist.
19. The method of claim 10, wherein the IAP antagonist is a monovalent IAP antagonist.
20. The method of claim 10, wherein the infection is caused by HBV.
21. The method of claim 10, wherein the infection is caused by HIV.
22. The method of claim 10, wherein the infection is caused by HTLV.
23. The method of claim 11, wherein the infection is caused by *Mycobacteria tuberculosis* (TB).
24. The method of claim 11, wherein the infection is caused by *Legionella pneumophila*.

* * * * *